(12) United States Patent
Chiba et al.

(10) Patent No.: US 9,376,506 B2
(45) Date of Patent: Jun. 28, 2016

(54) METHOD FOR PRODUCING SIALIC-ACID-CONTAINING SUGAR CHAIN

(75) Inventors: Yasunori Chiba, Ibaraki (JP); Yoshie Takahashi, Ibaraki (JP); Hisashi Narimatsu, Ibaraki (JP); Kazuhiro Fukae, Osaka (JP)

(73) Assignee: GLYTECH, INC., Kyoto (JP)

( * ) Notice: Subject to any disclaimer, the term of this patent is extended or adjusted under 35 U.S.C. 154(b) by 0 days.

(21) Appl. No.: 14/002,645

(22) PCT Filed: Feb. 27, 2012

(86) PCT No.: PCT/JP2012/054727
§ 371 (c)(1),
(2), (4) Date: Nov. 13, 2013

(87) PCT Pub. No.: WO2012/121041
PCT Pub. Date: Sep. 13, 2012

(65) Prior Publication Data
US 2014/0066617 A1    Mar. 6, 2014

(30) Foreign Application Priority Data

Mar. 4, 2011    (JP) .................................. 2011-047378

(51) Int. Cl.
| | | |
|---|---|---|
| C12P 19/18 | (2006.01) | |
| C12N 15/09 | (2006.01) | |
| C12N 15/52 | (2006.01) | |
| C12P 19/04 | (2006.01) | |
| C08B 37/00 | (2006.01) | |
| C12P 21/00 | (2006.01) | |

(52) U.S. Cl.
CPC ............ *C08B 37/0063* (2013.01); *C08B 37/006* (2013.01); *C12N 15/52* (2013.01); *C12P 19/04* (2013.01); *C12P 19/18* (2013.01); *C12P 21/005* (2013.01); *C12Y 204/99* (2013.01); *C12N 15/09* (2013.01)

(58) Field of Classification Search
None
See application file for complete search history.

(56) References Cited

U.S. PATENT DOCUMENTS

| 6,458,574 B1 | 10/2002 | Selden et al. | |
|---|---|---|---|
| 2006/0009421 A1 | 1/2006 | Kajihara et al. | |
| 2009/0018327 A1* | 1/2009 | Nishimura | C12P 19/32 536/123.13 |

FOREIGN PATENT DOCUMENTS

| EP | 1 577 324 | 9/2005 |
|---|---|---|
| EP | 2 752 425 | 7/2014 |
| WO | WO2004/058824 A1 | 7/2004 |

OTHER PUBLICATIONS

Liu et al "Chemo-enzymatic synthesis of trimeric sialyl Lewisx pentadecasaccharide" Can J Chem 2002 80 540-545.*
Harduin-Lepers "The human sialyltransferase family" Biochimie 83 (2001) 727-737.*
Invitrogen (Bacterial Alkaline Phosphatase 2005 pp. 1-2).*
Brenda Information for EC 2.4.99.1—Retrieved from < http://www.brenda-enzymes.org/enzyme.php?ecno=2.4.99.1 > on Sep. 30, 2015.*
Product Information for Cytidine-5'-monophospho-N-acetylneuraminic acid sodium—Sigma Aldrich. Retrieved from < http://www.sigmaaldrich.com/catalog/product/sigma/c8271?lang=en&region=US > on Oct. 1, 2015.*
English Translation of International Preliminary Report on Patentability Chapter I for PCT/JP2012/054727 mailed on Sep. 10, 2013.
International Search Report for PCT/JP2012/054727 mailed on Jun. 5, 2012.
Joziasse et al, "Branch Specificity of Bovine Colostrum CMP-Sialic Acid: Galβ1→4GlcNAc-R α2→6-Sialyltransferase. Sialylation of Bi-, Tri-, and Tetraantennary Oligosaccharides and Glycopeptides of the N-Acetyllactosamine Type." J. Biol. Chem., 262(5):2025-2033 (1987).
Kleineidam et al., "Studies on the inhibition of sialyl—and galactosyltransferase." Glycoconj. J., 14:57-66 (1997).
Krzewinski-Recchi et al., :Identification and functional expression of a second human β-galactoside α2,6-sialyltransferase, ST6Gal II. Eur. J. Biochem., 270:950-961 (2003).

(Continued)

*Primary Examiner* — Suzanne M Noakes
(74) *Attorney, Agent, or Firm* — Foley & Lardner LLP

(57) ABSTRACT

[Problem to be Solved]
The importance of sugar chains having α2,3- or α2,6-linked sialic acid at their non-reducing ends is known. Industrial production has been demanded for these sugar chain compounds. Particularly, the production of glycoprotein drugs or the like inevitably requires producing in quantity sugar chains having homogeneous structures by controlling the linking pattern (α2,6-linkage or α2,3-linkage) of sialic acid. Particularly, a triantennary or tetraantennary N-type complex sugar chain having sialic acid at each of all non-reducing ends is generally considered difficult to chemically synthesize. There has been no report disclosing that such a sugar chain was chemically synthesized. Furthermore, these sugar chains are also difficult to efficiently prepare enzymatically.
[Solution]
The present inventors have newly found the activity of sialyltransferase of degrading sialic acid on a reaction product in the presence of CMP and also found that formed CMP can be degraded enzymatically to thereby efficiently produce a sialic acid-containing sugar chain. The present inventors have further found that even a tetraantennary N-type sugar chain having four α2,6-linked sialic acid molecules, which has previously been difficult to synthesize, can be prepared at high yields by one-pot synthesis comprising the elongation reaction of a biantennary sugar chain used as a starting material without performing purification after each enzymatic reaction.

6 Claims, 9 Drawing Sheets

(56) References Cited

OTHER PUBLICATIONS

Liu et al, "Chemo-enzymatic synthesis of trimeric sialyl Lewis$^x$ pentadecasaccharide." Can. J. Chem., 80(6):540-545 (2002).

Miyazaki et al., "CMP substitutions preferentially inhibit polysialic acid synthesis." Glycobiology, 18(2):187-194 (2008).

Takashima et al., "Glycobiology and Extracellular Matrices: Characterization of the Second Type of Human β-Galactoside α 2,6-Sialyltransferase (ST6Gal II), Which Sialylates Gal β1,4GlcNAc Structures on Oligosaccharides Preferentially: Genomic Analysis of Human Sialyltransferase Genes." J. Biol. Chem., 277:45719-45728 (2002).

Takeuchi et al., "Comparative Study of the Asparagine-linked Sugar Chains of Human Erythropoietins Purified from Urine and the Culture Medium of Recombinant Chinese Hamster Ovary Cells." J. Biol. Chem., 263(8):3657-3663 (1988).

Thomas et al, "Enzymatic synthesis of N-linked oligosaccharides terminating in multiple sialyl-Lewis$^x$ and GalNAc-Lewis$^x$ determinants: clustered glycosides for studying selectin interactions." Carbohydr. Res., 306(3):387-400 (1998).

Tsuda et al., "The role of carbohydrate in recombinant human erythropoietin." Eur J Biochem., 188(2):405-411 (1990).

Van Den Eijnden et al., "Specificity in the Enzymic Transfer of Sialic Acid to the Oligosaccharide Branches of Bi—and Triantennary Glycopeptides of $\alpha_1$-Acid Glycoprotein." Biochem Biophys Res Commun., 92(3):839-845 (1980).

Yamamoto et al., "A β-galactoside α2,6-sialyltransferase produced by a marine bacterium, *Photobacterium leiognathi* JT-SHIZ-145, is active at pH 8." Glycobiology, 17(11):1167-1174 (2007).

Yamamoto et al., "Mass Production of Bacterial α2,6-Sialyltransferase and Enzymatic Syntheses of Sialyloligosaccharides." Biosci. Biotechnol. Biochem., 62(2):210-214 (1998).

Extended European Search Report for European Patent Application No. 12754383.3, dated May 6, 2015, 22 pages.

Wu, Z.L. et al.: "Universal phosphatase-coupled glycosyltransferase assay", G: Ycobiology, vol. 21, No. 6, Nov. 15, 2010, pp. 727-733, XP002733711.

Shimma et al., "Construction of a Library of Human Glycosyltransferases Immobilized in the Cell Wall of *Saccharomyces cerevisiae*", Appl Environ Microbial, Nov. 2006, 72(11): 7003-7012.

\* cited by examiner

METHOD FOR PRODUCING SIALIC-ACID-CONTAINING SUGAR CHAIN

CROSS-REFERENCE TO RELATED APPLICATIONS

This application is the U.S. national stage application under 35 U.S.C. §371 of International Patent Application No. PCT/JP2012/054727, filed on Feb. 27, 2012, which claims priority to Japanese Application No. 2011-047378, filed on Mar. 4, 2011, which are incorporated herein by reference in their entirety.

TECHNICAL FIELD

The present invention relates to a method for synthesizing a sugar chain that is applicable to drugs such as glycoproteins, standards for analytical instruments, scientific reagents, sugar chain arrays, etc.

BACKGROUND ART

A large number of previous studies have revealed that sugar chain structures bonded to proteins play an important functional role in the biological activities of the proteins. The sugar chain is also called the "face of the cell". The sugar chain expressed on cell surface is known to participate in cell-cell interaction or signaling, development or differentiation, fertilization, cancer metastasis, etc. As for modifications of sugar chains in mammals, Asn-linked, mucin-type, proteoglycan-type glycosylation and others are typically well-known. These modifications form their respective unique sugar chain structures through distinctive biosynthesis pathways. Sugars such as fucose or sialic acid are known to be added to the non-reducing ends of such sugar chain structures.

The sialic acid is a generic name for amino group- or hydroxy group-substituted compounds of neuraminic acid, which is a special nonose having amino and carboxy groups. N-acetylneuraminic acid (Neu5Ac) having an acetylated amino group at position 5 is probably the most predominant form in the nature. Various structures such as N-glycolylneuraminic acid having a glycolyl-modified amino group at position 5 or deamino-neuraminic acid KDN are also known.

Reportedly, the sialic acid-containing sugar chain is found not only in mammals including humans and mice but in vertebrates, echinoderms, and even protists or some bacteria having gram-negative pathogenicity. This sialic acid-containing sugar chain is produced via sialyltransferase. The sialyltransferase employs sialic acid added to cytidine monophosphate (CMP) as a substrate donor to transfer the sialic acid to, for example, position 3 or 6 of galactose, position 6 of N-acetylgalactosamine, or position 8 of another sialic acid via an aldehyde group present at position 2 of the sialic acid donor. For example, the enzyme transferring sialic acid to position 3 of galactose is called $\alpha$-2,3-sialyltransferase; the enzyme transferring sialic acid to position 6 of galactose or N-acetylgalactosamine is called $\alpha$-2,6-sialyltransferase; and the enzyme transferring sialic acid to position 8 of another sialic acid is called $\alpha$-2,8-polysialyltransferase. Of these enzymes, the $\alpha$-2,6-sialyltransferase is known as enzymes ST6Gal-I and ST6Gal-II transferring sialic acid to position 6 of galactose and enzymes ST6GalNAc-I, ST6GalNAc-II, ST6GalNAc-III, and ST6GalNAc-IV transferring sialic acid to position 6 of N-acetylgalactosamine, in humans.

ST6Gal-I recognizes a N-acetyllactosamine structure (Gal$\beta$1-4GlcNAc), which is N-acetylglucosamine having galactose linked to position 4, as a substrate acceptor and therefore modifies the non-reducing end structures of some glycolipids or N-linked sugar chains. Its specificity for the substrate acceptor has been analyzed mainly using biantennary or triantennary N-linked sugar chains. According to the report, the sialic acid tends to be transferred to lactosamine on the antenna of $\alpha$1,3-linked mannose (see Non Patent Literature 1). As for the preparation of the biantennary or triantennary N-linked sugar chains, these sugar chains are difficult to efficiently produce in quantity because, for example: glycosyltransferase substrates are rarely extracted from natural products; and a large-scale preparation method for the enzyme has not yet been established.

Meanwhile, $\alpha$2,6-sialic acid transfer reaction for tetraantennary N-linked sugar chains has been studied using bovine-derived ST6Gal-I. Of four N-acetyllactosamine structures in the sugar chain, the N-acetyllactosamine structure $\beta$1,2-linked to $\alpha$1,3-linked mannose is most susceptible to sialic acid transfer, followed by the N-acetyllactosamine structure $\beta$1,4-linked to $\alpha$1,3-linked mannose and further, either of two N-acetyllactosamine structures added to $\alpha$1,6-linked mannose, though no product containing four sialic acid molecules has been found (see Non Patent Literature 2). Human ST6Gal-I and, also ST6Gal-II, have been reported to have substrate specificity (see Non Patent Literatures 3 and 4). However, no study has been made on sialylation with tetraantennary N-linked sugar chains as acceptor substrates.

According to the reports, the product inhibition of ST6Gal-I by CMP is 49% inhibition (see Non Patent Literature 5) or 71% inhibition (see Non Patent Literature 6) by 0.25 mM CMP.

Meanwhile, *Photobacterium damsela* JT0160 (see Non Patent Literature 7), *Photobacterium leiognathi* JT-SHIZ-145 (see Non Patent Literature 8), and the like have been reported as bacterium-derived $\alpha$2,6-sialyltransferase. None of them, however, have been studied on sialylation with tetraantennary N-linked sugar chains as acceptor substrates.

As for $\alpha$2,3-sialic acid transfer reaction for tetraantennary N-linked sugar chains, tetraantennary N-linked sugar chains containing four $\alpha$2,3-linked sialic acid molecules are added to glycoproteins such as erythropoietin (EPO) (see Non Patent Literature 9). According to the report, such sialylation contributes to the stability of the glycoproteins in blood (see Non Patent Literature 10). Although these structures also occur naturally, there has been no case reporting that the tetraantennary N-linked sugar chains containing four $\alpha$2,3-linked sialic acid molecules were actually prepared in large amounts. This is because: EPO or the like used as a starting material is difficult to prepare in large amounts in terms of cost; and the asialo tetraantennary N-linked sugar chains used as acceptors in enzymatic synthesis are also difficult to inexpensively prepare from other natural products. Also, the glycoprotein EPO is known to have, for example, tetraantennary N-linked sugar chains containing $\alpha$2,3 and $\alpha$2,6 linkages together (see Non Patent Literature 11).

It has been reported as to the linking pattern of sialic acid linked to N-type sugar chains in antibody drugs or glycoprotein drugs such as cytokines that proteins having $\alpha$2,6-linked sialic acid disappear from blood faster than proteins having $\alpha$2,3-linked sialic acid. For clearance from blood, glycoproteins are incorporated into cells through in vivo binding to lectin molecules and finally metabolized. Thus, the glycoproteins having $\alpha$2,6-linked sialic acid can be expected to be incorporated in an organ-specific manner through binding to specific lectin molecules and also to be exploited in drug delivery. Also, glycoproteins are known to be excreted into urine in the kidney, depending on molecular sizes. Reportedly, the apparent molecular size of erythropoietin increases with increase in the number of antennas in its sugar chain, leading to slow clearance from blood. Thus, the synthesis of sugar chains having α2,3-linked and/or α2,6-linked sialic acid, particularly, tetraantennary N-type sugar chains having four molecules of α2,3-linked and/or α2,6-linked sialic acids can be expected to applicable to the production of glycoprotein drugs differing in the efficiency of uptake into an organ.

Human influenza virus recognizes, for its infection, α2,6-linked sialic acid in sugar chains expressed on cell surface, whereas bird-derived influenza virus recognizes α2,3-linked sialic acid for its infection. Many viruses, also including the influenza virus, start to infect cells by recognizing the sugar chain structures of the cells to be infected. In this regard, the binding specificity of these viruses must be examined using various sugar chains. Thus, sugar chains having α2,3- or α2,6-linked sialic acid may serve as a material for study on the binding specificity of such viruses and be applicable to, for example, the detection of the viruses.

CITATION LIST

Non Patent Literature

Non Patent Literature 1: van den Eijnden D H et al., Biochem Biophys Res Commun., 92 (3), 839-45 (1980)
Non Patent Literature 2: Joziasse et al., JBC, 262, 2025-2033 (1987)
Non Patent Literature 3: Takashima et al., JBC, 277, 45719-45728 (2002)
Non Patent Literature 4: Krzewinski-Recchi et al., EJB, 270, 950-961 (2003)
Non Patent Literature 5: Miyazaki T et al., Glycobiology, 18, 187-194 (2008)
Non Patent Literature 6: Kleineidam et al., Glycoconj. J., 14, 57-66 (1997)
Non Patent Literature 7: Yamamoto T et al., BBB, 62, 210-214 (1998)
Non Patent Literature 8: Yamamoto T et al., Glycobiology, 17, 1167-1174 (2007)
Non Patent Literature 9: Takeuchi et al., J. Biol. Chem., 263 (8), 3657-63 (1988)
Non Patent Literature 10: Tsuda et al., Eur J Biochem., 188 (2), 405-11 (1990)
Non Patent Literature 11: Takeuchi et al., J. Biol. Chem., 263 (8), 3657-63 (1988)

SUMMARY OF INVENTION

Technical Problem

The importance of sugar chains having α2,3- or α2,6-linked sialic acid at their non-reducing ends is known. Although these sugar chain compounds may occur naturally, their industrial production has been demanded because of the problems of extraction from natural products, such as the scarcity, difficult availability, and safety of the natural products. Particularly the production of antibody drugs or glycoprotein drugs such as cytokines or study on the binding specificity of viruses, or the like, inevitably requires producing in quantity sugar chains having homogeneous structures by controlling the linking pattern (α2,6-linkage or α2,3-linkage) of sialic acid. Particularly, a triantennary or tetraantennary N-type complex sugar chain having sialic acid at each of all non-reducing ends is generally considered difficult to chemically synthesize. There has been no report disclosing that, for example, a tetraantennary N-type complex sugar chain having α2,6-linked sialic acid at each of all non-reducing ends was chemically synthesized. Furthermore, these sialylated triantennary or tetraantennary sugar chains are enzymatically difficult to efficiently prepare.

Solution to Problem

The present inventors have newly found the activity of sialyltransferase of degrading sialic acid on a reaction product in the presence of CMP and also found that formed CMP can be degraded enzymatically to thereby efficiently produce a sialic acid-containing sugar chain. The present inventors have further found that even a tetraantennary N-type sugar chain having four α2,6-linked sialic acid molecules, which has previously been difficult to synthesize, can be prepared in high yields by one-pot synthesis comprising the elongation reaction of a biantennary sugar chain used as a starting material without performing purification after each enzymatic reaction.

Specifically, the present invention relates to a method for producing a sialylated second sugar chain or a derivative thereof, comprising reacting a first sugar chain or a derivative thereof with CMP-sialic acid in the presence of sialyltransferase and phosphatase to transfer sialic acid to a non-reducing end of the first sugar chain or a derivative thereof.

In this context, according to one embodiment of the method for producing a sialylated second sugar chain or a derivative thereof of the present invention, the first sugar chain or a derivative thereof is a triantennary or tetraantennary N-linked complex sugar chain or a derivative thereof.

According to one embodiment of the method for producing a sialylated second sugar chain or a derivative thereof of the present invention, the first sugar chain or a derivative thereof is a compound represented by the following formula:

[Formula 1]

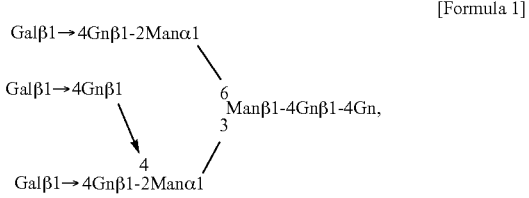

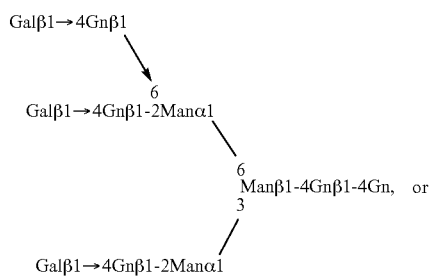

-continued

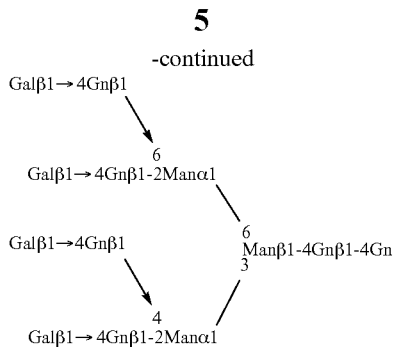

wherein Gn represents N-acetylglucosamine, Man represents mannose, and Gal represents galactose (the same holds true for the description below in the present specification; in the present specification, N-acetylglucosamine is also referred to as GlcNAc)
or a derivative thereof.

According to one embodiment of the method for producing a sialylated second sugar chain or a derivative thereof of the present invention, the sialylated second sugar chain or a derivative thereof is a triantennary or tetraantennary N-linked complex sugar chain, wherein the sugar chain is a compound having sialic acid at each of all non-reducing ends or a derivative thereof.

According to one embodiment of the method for producing a sialylated second sugar chain or a derivative thereof of the present invention, the sialylated second sugar chain or a derivative thereof is a compound represented by the following formula:

[Formula 2]

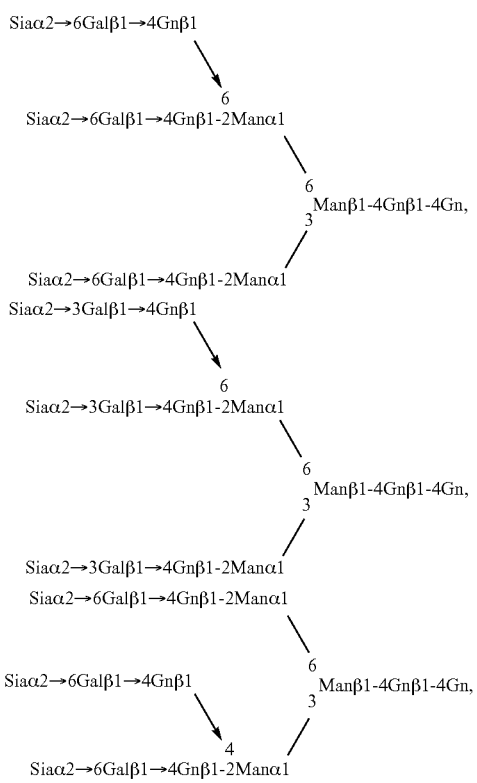

-continued

[Formula 3]

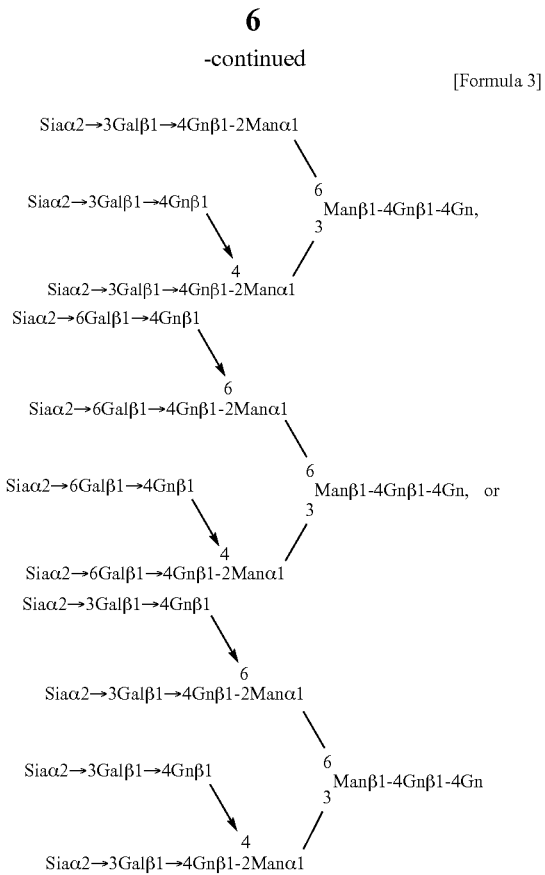

wherein Gn represents N-acetylglucosamine, Man represents mannose, Gal represents galactose, and Sia represents sialic acid (the same holds true for the description below in the present specification; in the present specification, N-acetylglucosamine is also referred to as GlcNAc)
or a derivative thereof.

An alternative aspect of the present invention relates to a method for producing a sialylated sugar chain or a derivative thereof, comprising the following steps:
(a) performing one or more time(s) a step of reacting a sugar chain represented by the following formula:

[Formula 4]

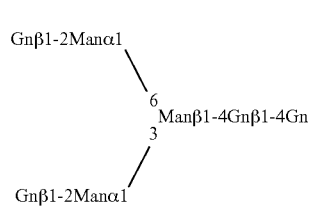

or a derivative thereof with UDP-sugar serving as a substrate of glycosyltransferase in the presence of the glycosyltransferase; and
(b) reacting the product of the step (a) with CMP-sialic acid in the presence of sialyltransferase and phosphatase.

A further alternative aspect of the present invention relates to a method for producing a sugar chain sialylated at its non-reducing end or a derivative thereof, comprising the following steps:
(a) reacting an agalacto biantennary complex sugar chain or a derivative thereof with UDP-GlcNAc in the presence of MGAT4 and MGAT5;

(b) reacting the product of the step (a) with UDP-Gal in the presence of β4GalT1; and (c) reacting the product of the step (b) with CMP-sialic acid in the presence of sialyltransferase and phosphatase.

According to one embodiment of the method for producing a sialylated sugar chain or a derivative thereof of the present invention, the sialyltransferase is α2,6-sialyltransferase.

According to one embodiment of the method for producing a sialylated sugar chain or a derivative thereof of the present invention, the sialyltransferase is human-derived sialyltransferase.

According to one embodiment of the method for producing a sialylated sugar chain or a derivative thereof of the present invention, the sialyltransferase is ST6Gal-I.

According to one embodiment of the method for producing a sialylated sugar chain or a derivative thereof of the present invention, the CMP-sialic acid is CMP-Neu5Ac.

According to one embodiment of the method for producing a sialylated sugar chain or a derivative thereof of the present invention, the phosphatase is alkaline phosphatase.

According to one embodiment of the method for producing a sialylated sugar chain or a derivative thereof of the present invention, the phosphatase is *E. coli*-derived alkaline phosphatase.

A further alternative aspect of the present invention relates to a compound having sialic acid at each of all non-reducing ends of a tetraantennary N-linked complex sugar chain or a derivative thereof.

A further alternative aspect of the present invention relates to a compound having α2,6-linked sialic acid at each of all non-reducing ends of a tetraantennary N-linked complex sugar chain or a derivative thereof.

A further alternative aspect of the present invention relates to a compound represented by the following formula:

[Formula 5]

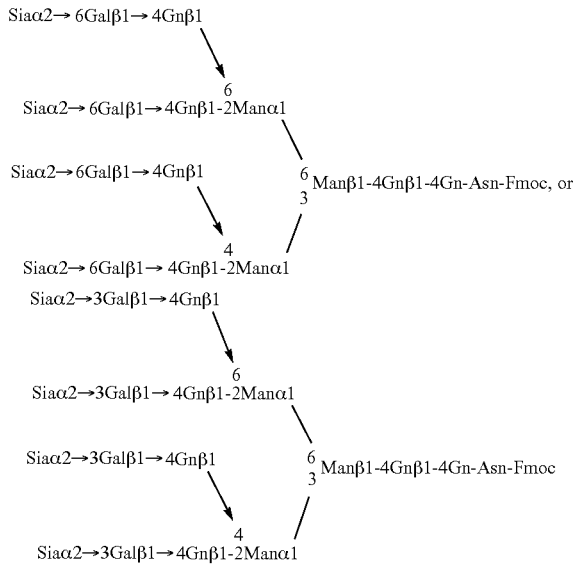

Advantageous Effects of Invention

The method of the present invention can more efficiently produce a sialic acid-containing sugar chain using sialyltransferase than ever before. Particularly, the method of the present invention can efficiently produce even a sialic acid-containing triantennary or tetraantennary complex sugar chain (including glycoamino acids and glycopeptides) in which sialic acid is linked to each of all non-reducing ends of the antennas, which has previously been difficult to produce. In addition, the method of the present invention can achieve convenient production in high yields through one-pot synthesis reaction and can achieve also the quantity production of these sugar chains, which has previously been difficult to achieve.

DESCRIPTION OF EMBODIMENTS

Figure 1:
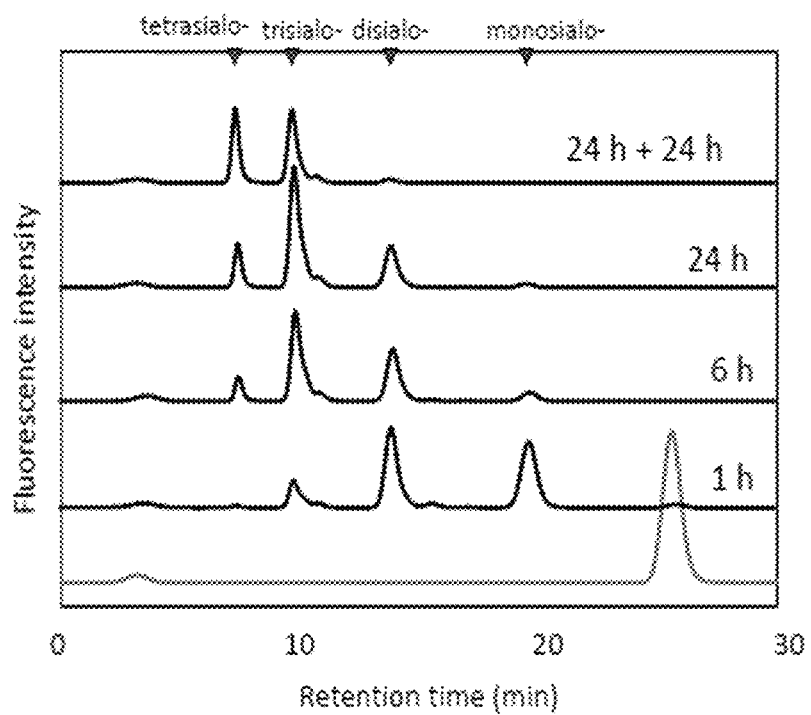
FIG. 1 shows an HPLC chart of each reaction product obtained by 0-hour, 1-hour, 6-hour, or 24-hour (from bottom to top) reaction at 37° C. after addition of ST6Gal-1 to a solution containing NA4-Fmoc as a tetraantennary complex sugar chain and CMP-NeuAc or by the further addition of CMP-NeuAc and ST6Gal-1 to the solution after 24 hours and subsequent 24-hour reaction (topmost). The terms "tetrasialo", "trisialo", "disialo", and "monosialo" shown in the upper part of the chart depict the retention times (min) of (α2,6)tetrasialo-NA4-Fmoc, (α2,6)trisialo-NA4-Fmoc, (α2,6)disialo-NA4-Fmoc, and (α2,6)monosialo-NA4-Fmoc, respectively, in the HPLC chart.

In the present specification, the "sialic acid" is a generic name for the family of amino group- or hydroxy group-substituted derivatives of neuraminic acid. In this context, the "neuraminic acid" is a special nonose having intramolecular amino and carboxyl groups and is represented by the following formula:

[Formula 6]

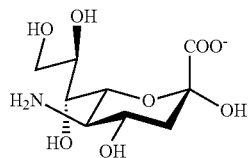

In the structure of the sialic acid, the acetylation, glycolylation, or the like of the amino group is known as the substitution of the amino group in the neuraminic acid described above. In addition, for example, deamination (elimination of the amino group) is also known. Acetylation, methylation, phosphorylation, lactylation, or the like is known as the substitution of the hydroxy group, though the substitution of the present invention is not limited thereto.

In the present specification, the sialic acid to be transferred is preferably N-acetylneuraminic acid (Neu5Ac), which is most abundant in the nature, or N-glycolylneuraminic acid (Neu5Gc), which is second abundant in the nature, from the viewpoint of producing naturally occurring glycoproteins or their sugar chains. N-acetylneuraminic acid is more preferred, particularly, from the viewpoint of producing naturally occurring glycoproteins as human glycoproteins or their sugar chains.

In the present specification, the "CMP-sialic acid" means cytidine-5'-monophospho-sialic acid and refers to a compound having a structure in which the hydroxy group at position 2 of sialic acid is dehydration-condensed with the phosphate group of cytidine monophosphate (CMP). Examples of the CMP-sialic acid with more specifically defined sialic acid include CMP-N-acetylneuraminic acid (CMP-Neu5Ac) and CMP-N-glycolylneuraminic acid (CMP-Neu5Gc). In the present specification, the CMP-sialic acid used in the present invention is preferably CMP-N-acetylneuraminic acid (CMP-Neu5Ac) or CMP-N-glycolylneuraminic acid (CMP-Neu5Gc) from the viewpoint of producing naturally occurring glycoproteins or their sugar chains, more preferably CMP-N-acetylneuraminic acid (CMP-Neu5Ac), particularly, from the viewpoint of producing naturally occurring glycoproteins as human glycoproteins or their sugar chains.

In the present specification, the "sialyltransferase" is one type of glycosyltransferase and refers to an enzyme that catalyzes a reaction through which a sialic acid residue is transferred from CMP-sialic acid serving as a sugar donor (also referred to as a donor substrate) to a sugar chain structure serving as a sugar acceptor (also referred to as an acceptor substrate) (hereinafter, this reaction is referred to as "sialic acid transfer reaction"). The sialyltransferase is known to transfer sialic acid to a non-reducing end of a sugar chain. The sialic acid transfer reaction can be represented by the reaction formula shown below. In the case of using a sugar chain derivative instead of the sugar chain, the sugar chain in the formula can be replaced with the sugar chain derivative.

[Expression 1]

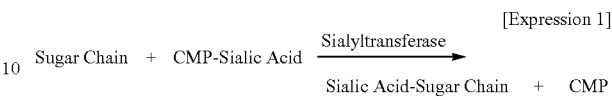

[wherein sialic acid-sugar chain represents a compound having sialic acid linked through a glycosidic linkage to a non-reducing end of the sugar chain.]

The sialyltransferase is known to transfer sialic acid to, for example, position 3 or 6 of galactose, position 6 of N-acetylgalactosamine, or position 8 of another sialic acid at a non-reducing end of the sugar chain. For example, the enzyme transferring sialic acid to position 3 of galactose is called α-2,3-sialyltransferase; the enzyme transferring sialic acid to position 6 of galactose or N-acetylgalactosamine is called α-2,6-sialyltransferase; and the enzyme transferring sialic acid to position 8 of another sialic acid is called α-2,8-polysialyltransferase.

For example, bacterium-derived sialyltransferase as well as rainbow trout- or mammal-derived sialyltransferase is known. Also, a protein having sialyltransferase-like activity has been found in plants. Mammal-derived sialyltransferase is preferred, particularly, from the viewpoint of producing naturally occurring glycoproteins as mammalian glycoproteins or their sugar chains. Human-derived sialyltransferase is more preferred from the viewpoint of producing naturally occurring glycoproteins as human glycoproteins or their sugar chains.

Human-derived α-2,6-sialyltransferase is known as, for example, enzymes ST6Gal-I (also referred to as ST6Gal1; the same holds true for the description below) and ST6Gal-II transferring sialic acid to position 6 of galactose and enzymes ST6GalNAc-I, ST6GalNAc-II, ST6GalNAc-III, and ST6GalNAc-IV transferring sialic acid to position 6 of N-acetylgalactosamine.

Human-derived α-2,3-sialyltransferase is known as, for example, enzymes ST3Gal-I to ST3Gal-VI transferring sialic acid to position 3 of galactose.

The sialyltransferase is preferably ST6Gal-I, ST6Gal-II, ST3Gal-I, ST3Gal-II, ST3Gal-III, ST3Gal-IV, ST3Gal-VI, ST6GalNAc-I, ST6GalNAc-II, ST6GalNAc-III, ST6GalNAc-IV, ST8Sia-II, ST8Sia-III, or ST8Sia-IV, particularly, from the viewpoint of producing naturally occurring glycoproteins or their sugar chains. Alternatively, ST6Gal-I, ST6Gal-II, ST3Gal-III, ST3Gal-IV, ST3Gal-VI, ST8Sia-II, ST8Sia-III, or ST8Sia-IV is preferred from the viewpoint of producing N-linked sugar chains.

In the present specification, the "sugar chain" refers to a compound having a linkage of one or more unit sugar(s) (monosaccharide and/or derivative thereof). In the case of a sugar chain having a linkage of two or more unit sugars, the unit sugars are bonded by dehydration condensation through a glycosidic linkage therebetween. Examples of such a sugar chain include, but not limited to, monosaccharides and polysaccharides (glucose, galactose, mannose, fucose, xylose, N-acetylglucosamine, N-acetylgalactosamine, sialic acid, and their complexes and derivatives) contained in vivo, and a wide range of other sugar chains such as degraded polysaccharides and sugar chains degraded or induced from complex biomolecules including glycoproteins, proteoglycans, glycosaminoglycans, and glycolipids. The sugar chain may be linear or branched.

In the present specification, the "sugar chain" also includes a compound having a modified substituent of a sugar chain. Examples thereof include, but not limited to, sugar chains such as sugar chains constituted by sugars having a carboxyl group (e.g., aldonic acid (e.g., D-gluconic acid, an oxidation product of D-glucose), which is carboxylic acid formed by oxidation at C-1 position, and uronic acid (e.g., D-glucuronic acid, an oxidation product of D-glucose), which is a carboxylic acid formed by the oxidation of a terminal carbon atom), sugars having an amino group or an amino group derivative (e.g., an acetylated amino group) (e.g., N-acetyl-D-glucosamine and N-acetyl-D-galactosamine), sugars having both amino and carboxyl groups (e.g., N-acetylneuraminic acid (sialic acid) and N-acetylmuramic acid), deoxidized sugars (e.g., 2-deoxy-D-ribose), sulfated sugars containing a sulfate group, and phosphorylated sugars containing a phosphate group.

In the present specification, the sugar chain is preferably a sugar chain that is found in the form of a glycoconjugate (glycopeptide (or glycoprotein), proteoglycan, glycolipid, etc.) in vivo, preferably a sugar chain bonded to a peptide (or protein) to form a glycopeptide (or glycoprotein) in vivo, for example, a N-linked sugar chain or an O-linked sugar chain, from the viewpoint of producing glycoproteins serving as drugs. The N-linked sugar chain is a generic name for sugar chains whose pattern of linking to a protein is the bond between an anomeric hydroxy group in N-acetylglucosamine at the reducing end of the sugar chain and the amino group (—NH$_2$) of an asparagine side chain through dehydration condensation. The O-linked sugar chain is a generic name for sugar chains whose pattern of linking to a protein is the bond between an anomeric hydroxy group at the reducing end of the sugar chain and the hydroxy group (—OH) of a serine or threonine side chain through dehydration condensation.

The N-linked sugar chain is also called an asparagine-linked sugar chain, a N-type sugar chain, or the like. The N-linked sugar chain is a group of sugar chains having Man$_3$-GlcNAc-GlcNAc as a core. Depending on the structures of sugar chains linked to Man in the core, the N-linked sugar chain is known to have a particular sugar chain structure called a high-mannose, complex, or hybrid type. Also, a multiantennary structure such as a biantennary, triantennary, or tetraantennary type is known as the branched structure of the N-linked sugar chain. These sugar chain structures are also described in, for example, Seikagaku Jiten (Encyclopedia of Biochemistry in English), 3rd ed., issued by Tokyo Kagaku Dojin Co., Ltd.

In the present specification, the first sugar chain or a derivative, i.e., the sugar chain or a derivative thereof serving as a sugar acceptor in the presence of sialyltransferase and phosphatase, is not particularly limited as long as the sugar chain or a derivative has, at its non-reducing end, a sugar chain structure serving as a sialyltransferase substrate. Many naturally occurring glycoproteins are known to contain branched sugar chain(s) having structure(s) in which sialic acid is linked to the non-reducing end of the complex- or hybrid-type N-linked sugar chain. The first sugar chain or a derivative thereof is preferably a N-linked complex sugar chain or a N-linked hybrid sugar chain, more preferably a N-linked complex sugar chain capable of having sialic acid at each of all non-reducing ends, from the viewpoint of producing these sugar chains. The branched structure is preferably a N-linked triantennary or tetraantennary sugar chain, which has previously been difficult to produce. A N-linked triantennary or tetraantennary complex sugar chain is more preferred.

In the present specification, the "first sugar chain or a derivative thereof" refers to a sugar chain or a derivative thereof that is used as a starting material compound (also referred to as a starting compound) in sialic acid transfer reaction and also refers to a sugar chain having, at at least one non-reducing end, a sugar chain structure serving as a sialyltransferase substrate. The "first sugar chain or a derivative thereof" used in the sialic acid transfer reaction is also referred to as a "sugar acceptor" or an "acceptor substrate", while the "CMP-sialic acid" is also referred to as a "sugar donor" or a "donor substrate". The "first sugar chain or a derivative thereof" used is preferably, for example, a compound having a sialyltransferase substrate structure at each non-reducing end of a branched sugar chain, or in other words, a compound having a completely sialic acid-deficient structure of the "sialylated second sugar chain or a derivative thereof" as the compound of interest. In the present specification, such a sugar chain is also referred to as an "asialo sugar chain", an "asialo form", or "asialo".

In the present specification, the asialo sugar chain is preferably, for example, a tetraantennary sugar chain represented by the formula shown below or a derivative thereof.

In the present specification, the asialo tetraantennary N-linked complex sugar chain or a derivative thereof is preferably, for example, a sugar chain represented by the following formula:

[Formula 7]

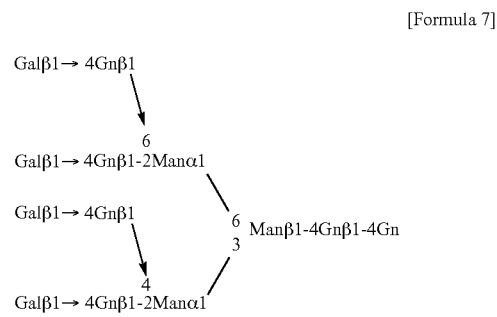

or a derivative thereof.

In the present specification, the asialo triantennary N-linked complex sugar chain or a derivative thereof is preferably, for example, a sugar chain represented by the following formula:

[Formula 8]

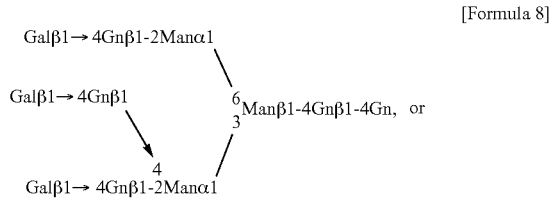

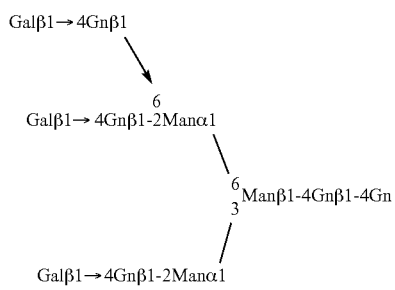

or a derivative thereof.

In the present specification, the asialo biantennary N-linked complex sugar chain or a derivative thereof is preferably, for example, a sugar chain represented by the following formula:

[Formula 9]

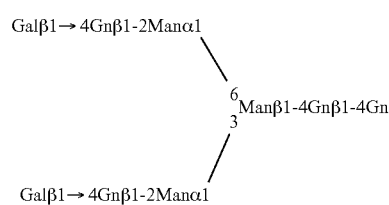

or a derivative thereof.

In addition to these sugar chains, a sugar chain having sialic acid linked through a glycosidic linkage to one or more position(s) in the non-reducing ends of each of the sugar chains, or a derivative thereof may be used as a sugar acceptor in the sialic acid transfer reaction of the present invention. Conventional methods rarely produce a multiantennary sugar chain having sialic acid at each of all non-reducing ends of the sugar chain. Even such a sugar chain obtained by the conventional methods can be converted to a sugar chain having sialic acid at each of all non-reducing ends by the sialic acid transfer reaction of the present invention. Examples of the sugar chain obtained by the conventional methods include compounds represented by the following formulas:

[Formula 10]

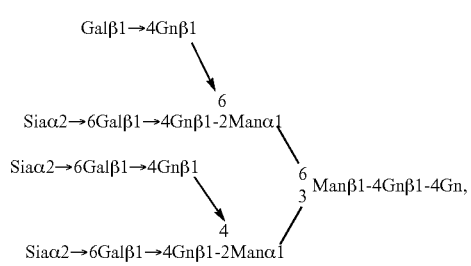

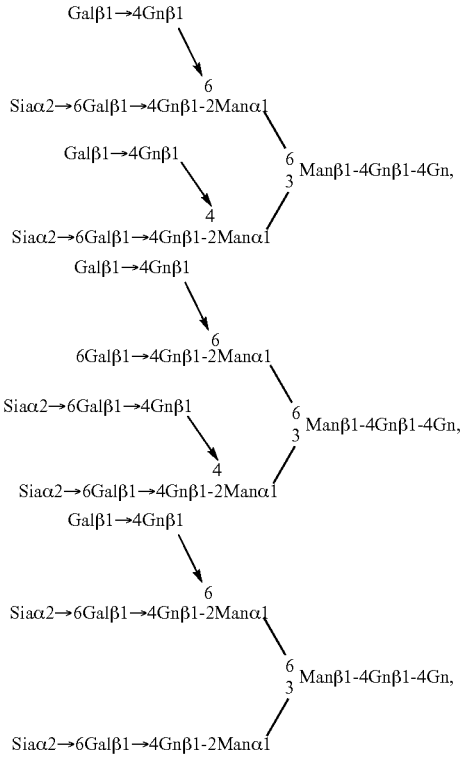

These compounds can be obtained by the conventional methods or may be also produced by adjusting the reaction time in the method of the present invention.

The sugar chain having sialic acid linked through a glycosidic linkage to one or more position(s) in its non-reducing ends, or a derivative thereof may be used as the first sugar chain or a derivative thereof, while sialyltransferase that forms a glycosidic linkage different from that of the sialic acid in the compound may be used. In such a case, a compound having different patterns of glycosidic linkages of sialic acid residues can be produced.

In the present specification, the "derivative of the sugar chain" also includes a compound having an additional compound linked to the reducing end of the sugar chain through dehydration condensation or the like. The "derivative of the sugar chain" is, for example, a compound further having R linked to N-acetylglucosamine at the reducing end of the sugar chain, as represented by the following formula:

[Formula 11]

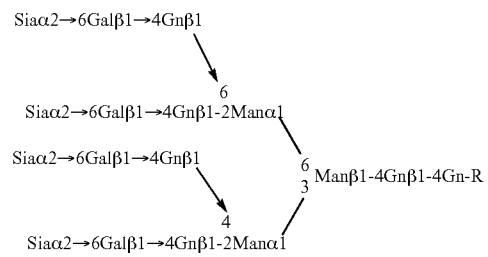

This sugar chain derivative is provided merely for illustrative purposes, and derivatives of other sugar chains can also be indicated by the sugar chains plus —R at the reducing ends of the sugar chains.

The derivative of the sugar chain also includes a sugar chain containing an amino acid, a peptide, a protein, a linker, a fluorescent group, a lipid, a low-molecular-weight compound, a radioactive compound, or the like as the R moiety at the reducing end. The amino acid includes not only natural amino acids but nonnatural amino acids such as amino acid variants and derivatives. The amino acid, the peptide, the protein, or the like may be protected, at some or all of functional groups such as hydroxy, amino, and carboxyl groups, with protective groups. Examples of the protective group for the hydroxy group can include methyl, benzyl, benzoyl, acetyl, trimethylsilyl (TMS), triethylsilyl (TES), and tert-butyldimethylsilyl (TBS or TBDMS) groups. Examples of the protective group for the amino group can include lipid-soluble protective groups including carbonate or amide protective groups such as 9-fluorenylmethoxycarbonyl (Fmoc), t-butyloxycarbonyl (Boc), benzyl, allyloxycarbonyl, and acetyl groups. In the case of introducing a lipid-soluble protective group, for example, an Fmoc group, this group can be introduced through reaction by the addition of 9-fluorenylmethyl-N-succinimidyl carbonate and sodium carbonate.

Examples of the protective group for the carboxyl group can include benzyl, allyl, and diphenylmethyl groups. These protective groups are provided merely for illustrative purposes, and the protective group of the present invention is not limited thereto. Since the sialyltransferase acts on the non-reducing end of the sugar chain, any adduct can be used for the reducing end of the sugar chain unless the adduct largely influences the sugar transfer reaction. The linker is useful for attaching the produced sugar chain to an amino acid, a protein, or the like. Examples thereof can include, but not limited to, —NH—(CO)—$(CH_2)_a$—$CH_2$—
(wherein a is any integer without limitations unless the linker functions of interest are inhibited, and preferably represents an integer of 0 to 4),
$C_{1-10}$ polymethylene, and —$CH_2$—$R_1$— (wherein $R_1$ represents a group formed by the elimination of one hydrogen atom from a group selected from the group consisting of alkyl, substituted alkyl, alkenyl, substituted alkenyl, alkynyl, substituted alkynyl, aryl, substituted aryl, a carbocyclic group, a substituted carbocyclic group, a heterocyclic group, and a substituted heterocyclic group). The fluorescent group is useful for use in the purification of the produced sugar chain, the test of the sugar chain, etc. Examples thereof can include dansyl, pyridylamino (PA), 2-aminobenzamide (2-AB), 2-aminobenzoic acid (2-AA), and 9-aminopyrene-1,4,6-trisulfonic acid (APTS) groups. Alternatively, the derivative of the sugar chain may contain, in any order, two or more adducts such as a sugar chain-amino acid and an additional linker added thereto, or a sugar chain and an amino acid linked via a linker.

In the present specification, the derivative of the sugar chain is preferably a sugar chain-amino acid, a glycosylated peptide, or a glycosylated protein, more preferably sugar chain-asparagine (also indicated by sugar chain-Asn) from the viewpoint of producing sugar chains of natural glycoproteins. A compound containing a protective group bonded to the sugar chain-asparagine (also indicated by sugar chain-Asn-$R_2$, wherein $R_2$ represents a protective group) is preferred from the viewpoint of using the produced sugar chain-asparagine in solid-phase synthesis. In addition to the lipid-soluble protective groups exemplified above, a protective group generally known by those skilled in the art can be used as the protective group. For example, sugar chain-asparagine-Fmoc (sugar chain-Asn-Fmoc) or sugar chain-asparagine-Boc (sugar chain-Asn-Boc), which is the sugar chain-asparagine having the lipid-soluble protective group Fmoc or Boc, or the like, is preferred.

In the present specification, the "sialylated second sugar chain or a derivative thereof" refers to a sugar chain or a derivative thereof that is a sialic acid transfer reaction product, and refers to a sugar chain having sialic acid at at least one non-reducing end or a derivative thereof. The "sialylated second sugar chain or a derivative thereof" is preferably a sugar chain having sialic acid at each of all non-reducing ends having a sialyltransferase substrate structure among non-reducing ends, or a derivative thereof. The "sialylated second sugar chain or a derivative thereof" is more preferably a sugar chain having sialic acid at each of all non-reducing ends or a derivative thereof.

In the present specification, the sialylated sugar chain or a derivative thereof may be defined in terms of the number of sialic acid molecule(s) linked to one sugar chain molecule. The sialylated sugar chain or a derivative thereof is referred to as "tetrasialo" when 4 sialic acid molecules are linked to 1 sugar chain molecule, as "trisialo" when 3 sialic acid molecules are linked to 1 sugar chain molecule, as "disialo" when 2 sialic acid molecules are linked to 1 sugar chain molecule, and as "monosialo" when 1 sialic acid molecule is linked to 1 sugar chain molecule. Alternatively, such a sialylated sugar chain or a derivative thereof is also referred to as a "tetrasialo sugar chain", a "tetrasialo form", or the like. For example, a compound having 4 sialic acid molecules linked to 1 tetraantennary sugar chain molecule can be called a "tetrasialo" "tetraantennary" sugar chain; a compound having 3 sialic acid molecules linked to 1 tetraantennary sugar chain molecule can be called a "trisialo" "tetraantennary" sugar chain; and a compound having 3 sialic acid molecules linked to 1 triantennary sugar chain molecule can be called a "trisialo" "triantennary" sugar chain.

In the present specification, the term "tetrasialo" includes any compound having 4 sialic acid molecules linked to 1 sugar chain molecule, regardless of the type of the glycosidic linkage between each sialic acid and the sugar chain, for example, a compound having ($\alpha$2,6) linkages as all glycosidic linkages, a compound having ($\alpha$2,3) linkages as all glycosidic linkages, and a compound having ($\alpha$2,6) linkages as some glycosidic linkages and ($\alpha$2,3) linkages as other glycosidic linkages. However, the term "($\alpha$2,6)tetrasialo" simply described in the present specification refers to a compound in which all of 4 sialic acid molecules are linked through ($\alpha$2,6) linkages to the sugar chain. The term "($\alpha$2,3) tetrasialo" simply described in the present specification refers to a compound in which all of 4 sialic acid molecules are linked through ($\alpha$2,3) linkages to the sugar chain. The pattern of the glycosidic linkage formed between the sialic acid and the non-reducing end of the "first sugar chain or a derivative thereof" by sialyltransferase is not particularly limited and is preferably an $\alpha$2,6, $\alpha$2,3, or $\alpha$2,8 linkage. When the "sialylated second sugar chain or a derivative thereof" has a plurality of sialic acid molecules at the non-reducing ends of the sugar chain, the glycosidic linkages formed between the sialic acid molecules and the non-reducing ends of the "first sugar chain or a derivative thereof" may have the same or different patterns.

In the present specification, the "sialylated second sugar chain or a derivative thereof" as a sialic acid transfer reaction product is preferably, for example, a sugar chain represented by the formula shown below or a derivative thereof.

The tetraantennary N-linked complex sugar chain having sialic acid at each of all non-reducing ends of the second sugar chain (in the present specification, also referred to as a tetrasialo tetraantennary N-linked complex sugar chain) as the "sialylated second sugar chain or a derivative thereof" is preferably, for example, a sugar chain represented by the following formula:

[Formula 12]

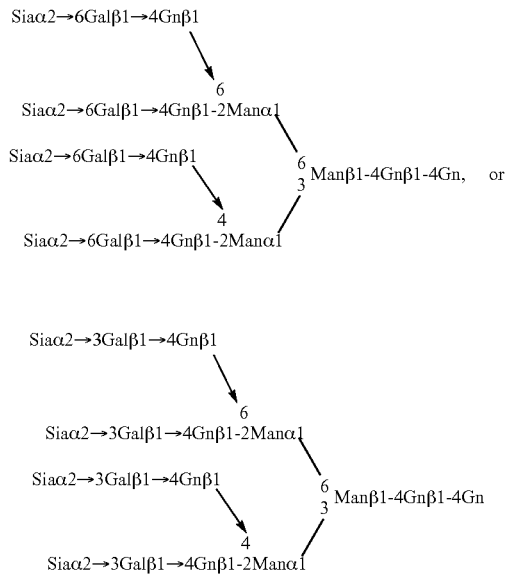

or a derivative thereof.

Alternatively, the triantennary N-linked complex sugar chain having sialic acid at each of all non-reducing ends of the second sugar chain (in the present specification, also referred to as a trisialo triantennary N-linked complex sugar chain) as the "sialylated second sugar chain or a derivative thereof" is preferably, for example, a sugar chain represented by the following formula:

[Formula 13]

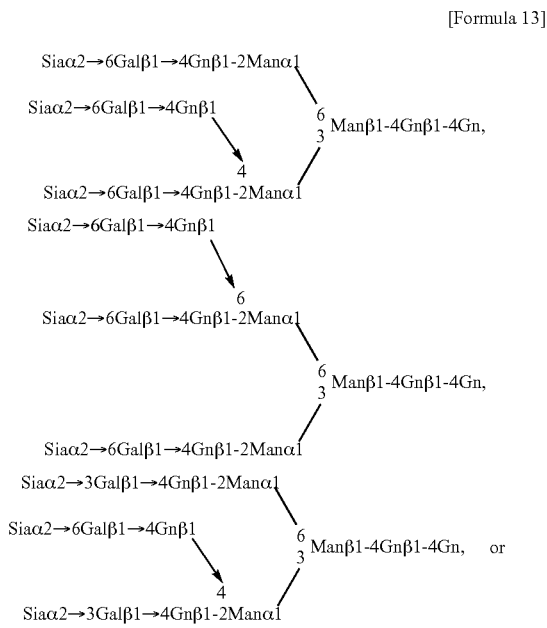

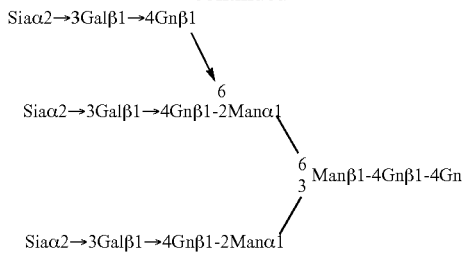

or a derivative thereof.

Alternatively, the biantennary N-linked complex sugar chain having sialic acid at each of all non-reducing ends of the second sugar chain (in the present specification, also referred to as a disialo biantennary N-linked complex sugar chain) as the "sialylated second sugar chain or a derivative thereof" is preferably, for example, a sugar chain represented by the following formula:

[Formula 14]

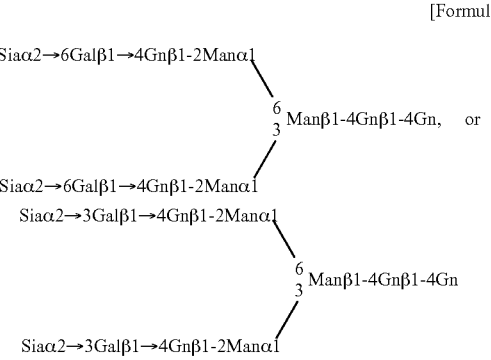

or a derivative thereof.

In this context, the N-linked complex sugar chain is known to be also found in the form of a compound having Fuc or Gn linked to any of the sugar chains described above. Such a compound is also included in the scope of the present invention. More specifically, it is known that: Fuc is α1,6-linked to Gn at a reducing end; Gn is β1,4-linked to position 4 of Man linked to Gn at a reducing end; and Fuc is α1,3 or α1,4-linked to Gn at a branching moiety. A compound having Gn(β1,4)Man or Gn(β1,2)Man instead of Gn(β1,6)Man as a linking pattern at the branching moiety of any of the sugar chains described above, a compound having Gn(β1,2)Man instead of Gn(β1,4)Man there as, and a sugar chain having glycosidic linkages differing in linking pattern, such as a compound having Sia(α2,3)Gal instead of some sialic acid-linked moieties Sia(α2,6)Gal or a compound having Sia(α2,6)Gal instead of some Sia(α2,3)Gal moieties are also included in the scope of the present invention.

In the present specification, the "phosphatase" refers to an enzyme that catalyzes a reaction through which phosphoric acid ester is hydrolyzed. The phosphatase is not particularly limited as long as the phosphatase has the activity of hydrolyzing phosphoric acid ester in CMP under reaction conditions for glycosyltransferase. For example, alkaline phosphatase, which is active under alkaline conditions, or acid phosphatase, which is active under acidic conditions, is known as the phosphatase. The alkaline phosphatase is known to be widely distributed throughout the body including the liver, the kidney, osteoblasts, the placenta, and the small intestine. The acid phosphatase is known to be stored in lysosomes and also found in various organs or plasma. For example, bacterium-derived, *E. coli*-derived, shrimp-derived, or mammal-derived phosphatase is known. For example, *E. coli*-derived alkaline phosphatase (BAP), bovine-derived alkaline phosphatase (CIP, CAP, or CIAP), and shrimp-derived alkaline phosphatase (SAP) are known.

The sialic acid transfer reaction in the present specification will be described.

The sialyltransferase used can be a commercially available product (α2,3-(N)-Sialyltransferase, Rat, Recombinant, *S. frugiperda*, α2,3-(O)-Sialyltransferase, Rat, Recombinant, *S. frugiperda*, α2,6-(N)-Sialyltransferase, Human, Recombinant *S. frugiperda*, Recombinant beta-galactoside-alpha-2,3-sialyltransferase, Recombinant beta-galactoside-alpha-2,6-sialyltransferase, etc.) or can be obtained by: obtaining a gene by PCR amplification or chemical gene synthesis on the basis of a publicly known gene sequence or amino acid sequence; inserting the obtained gene into an expression vector such as a plasmid; and obtaining the enzyme as a recombinant using an expression system of *E. coli*, yeast, insect cells, plant cells, animal cells, or the like. Alternatively, the sialyltransferase can be purified from a biological sample such as bovine small intestine tissue or cultured animal cells and used in the present invention. Those skilled in the art can produce the sialyltransferase by using any of the methods described in the present specification or appropriately modifying these methods.

The phosphatase used can also be a commercially available product, for example, Bacterial Alkaline Phosphatase (*E. coli*), Calf intestine Alkaline Phosphatase (CIP), or Alkaline Phosphatase from Shrimp (SAP) or can be produced appropriately.

The CMP-sialic acid used can also be a commercially available product, for example, cytidine-5'-monophospho-N-acetylneuraminic acid (disodium) or can be produced appropriately.

The reaction solvent used in the sialyltransferase reaction is not particularly limited as long as the solvent permits conditions under which the activity of the sialyltransferase is maintained. A stabilizer (e.g., bovine serum albumin), a surfactant, or the like may be added to the reaction solvent. For example, an aqueous solution containing 0.1 M Tris-HCl (pH 7.5), 1 mM $MnCl_2$, and 0.1% Triton X-100 can be used. Those skilled in the art can appropriately modify the reaction solvent for use.

The pH of the reaction solvent is not particularly limited within a range that maintains the activity of the sialyltransferase. The pH range optimal for the sialyltransferase is preferably on the order of 5 to 10, more preferably on the order of 7 to 8. The reaction solvent may be prepared at a slightly alkaline pH or an acidic pH, rather than neutral, in consideration of a range that maintains the activity of the phosphatase used.

The reaction temperature is not particularly limited as long as the temperature permits conditions under which the activity of the sialyltransferase is maintained. The temperature optimal for the enzyme is preferably around 37° C. The reaction temperature is preferably 10° C. to 40° C., more preferably 20° C. to 37° C., further preferably 25° C. to 37° C. 25° C. to 30° C. is preferred from the viewpoint of preventing CMP-sialic acid from being degraded by sialyltransferase.

The reaction time is not particularly limited as long as the time is sufficient for the progression of the sialic acid transfer reaction. Those skilled in the art can appropriately determine the reaction time. Particularly, in the case of transferring sialic acid to each non-reducing end of a multiantennary sugar chain, the reaction time can be set to preferably 8 hours to 48 hours, more preferably 16 to 24 hours.

During the reaction, the sugar donor CMP-sialic acid as well as phosphatase or sialyltransferase may be further added after reaction for a given time and then reacted. They may be added simultaneously or may be added separately at an appropriate time interval. For example, after 24-hour reaction, CMP-sialic acid and sialyltransferase may be further added and reacted for additional 24 hours.

In the present specification, the first sugar chain or a derivative thereof used can be purified and processed from a natural product, purified from a glycoprotein synthesized in an expression system, synthesized chemically or enzymatically, or the like. Alternatively, these products may be further subjected to, for example, sugar chain elongation reaction and then used in the reaction of the present invention. The sugar chain elongation reaction can involve: according to the glycosidic linkage pattern of the intended sugar chain structure, selecting an enzyme that catalyzes the formation of the glycosidic linkage; and elongating the sugar chain sequentially according to the order of linking of sugars constituting the sugar chain to produce the sugar chain of interest.

According to one aspect of the present invention, the multiantennary N-linked complex sugar chain used as a sugar chain serving as a sugar acceptor in the sialic acid transfer reaction or a derivative thereof is produced through sugar chain elongation reaction with a sugar chain represented by the following formula (hereinafter, referred to as an agalacto biantennary sugar chain) or a derivative thereof as a starting material:

[Formula 15]

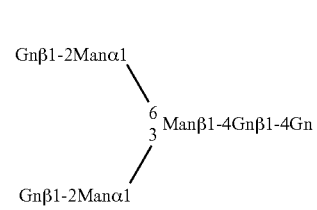

For example, agalacto biantennary sugar chain-Asn-Fmoc represented by the following formula can be used as a derivative of the above described sugar chain:

[Formula 16]

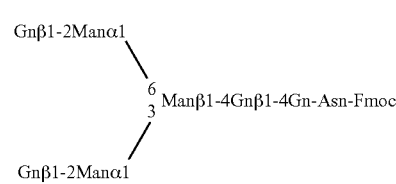

According to one aspect of the present invention, the tetraantennary N-linked complex sugar chain used as the first sugar chain or a derivative thereof can be produced by the steps of:

(a) reacting the agalacto biantennary sugar chain represented by the above described formula or a derivative thereof with UDP-GlcNAc in the presence of N-acetylglucosaminyltransferase; and (b) reacting the product of the step (a) with UDP-Gal in the presence of galactosyltransferase.

The N-acetylglucosaminyltransferase can be selected according to the glycosidic linkage that is formed between the sugar chain and the sugar to be transferred. For example, an enzyme that catalyzes the formation of a β1-6 linkage can be selected when the glycosidic linkage of interest is a β1-6 linkage. Alternatively, an enzyme that catalyzes the formation of a β1-4 linkage can be selected when the glycosidic linkage of interest is a β1-4 linkage. Examples of the enzyme that catalyzes the formation of a β1-6 linkage (β1,6-N-acetylglucosaminyltransferase) can include human MGAT5 and bovine GnT-V. Examples of the enzyme that catalyzes the formation of a β1-4 linkage (β1,4-N-acetylglucosaminyltransferase) can include human MGAT4a, human MGAT4b, and bovine GnT-Iva.

The galactosyltransferase can be selected according to the glycosidic linkage that is formed between the sugar chain and the sugar to be transferred. An enzyme that catalyzes the formation of a β1-4 linkage can be selected when the glycosidic linkage of interest is a β1-4 linkage. Examples of the enzyme can include β4GalT1, β4GalT2, and *Helicobacter pylori*-derived β1,4-galactosyltransferase.

In the case of producing a tetraantennary sugar chain represented by the following formula:

[Formula 17]

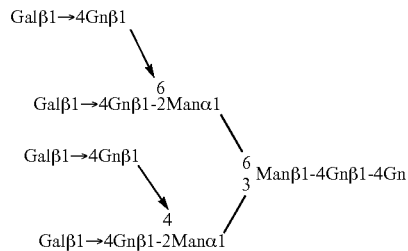

or a derivative thereof, the sugar chain or a derivative can be produced, for example, using MGAT4a and MGAT5 as N-acetylglucosaminyltransferase in the step (a) and β4GalT1 as galactosyltransferase in the step (b). The enzymes in this combination may be replaced with the enzymes exemplified above, etc., to produce the sugar chain of interest.

According to one aspect of the present invention, the triantennary N-linked complex sugar chain used as the first sugar chain or a derivative thereof can also be produced in the same way as in the tetraantennary sugar chain.

In the case of producing a triantennary sugar chain represented by the following formula:

[Formula 18]

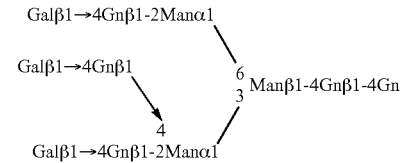

or a derivative thereof, the sugar chain or a derivative can be produced, for example, using MGAT4a as N-acetylglucosaminyltransferase in the step (a) and β4GalT1 as galactosyltransferase in the step (b).

Alternatively, in the case of producing a triantennary sugar chain represented by the following formula:

[Formula 19]

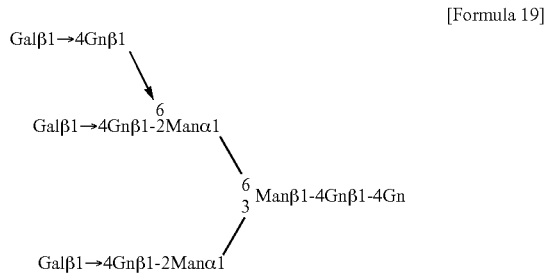

or a derivative thereof, the sugar chain or a derivative can be produced, for example, using MGAT5 as N-acetylglucosaminyltransferase in the step (a) and β4GalT1 as galactosyltransferase in the step (b). The enzymes in this combination may be replaced with the enzymes exemplified above, etc., to produce the sugar chain of interest.

According to one aspect of the present invention, the biantennary N-linked complex sugar chain used as the first sugar chain or a derivative thereof can be produced by the step of: (b) reacting the agalacto biantennary sugar chain represented by the above described formula with UDP-Gal in the presence of galactosyltransferase.

The galactosyltransferase is the same as in the tetraantennary N-linked complex sugar chain.

According to one aspect of the present invention, the first sugar chain or a derivative thereof may be a compound containing the tetraantennary N-linked complex sugar chain or a derivative thereof and further containing fucose or N-acetylglucosamine added thereto. In such a case, this sugar may be added using fucosyltransferase or N-acetylglucosaminyltransferase.

According to one aspect of the present invention, the first sugar chain or a derivative thereof can be produced through sugar chain elongation reaction with the above described agalacto biantennary sugar chain as a starting material or may also be produced by necessary sugar chain elongation reaction, for example, with a chicken egg-yolk derived glycopeptide containing an agalacto biantennary sugar chain or PA-agalacto biantennary sugar chain (sold by Takara Bio Inc.) as a starting material.

According to one aspect of the present invention, the first sugar chain or a derivative thereof can be produced through sugar chain elongation reaction that involves isolating and purifying a sugar chain or a derivative thereof as a sugar chain elongation reaction product after each sugar chain elongation reaction; and then using the resulting sugar chain or derivative thereof in next sugar chain elongation reaction.

According to one aspect of the present invention, sialic acid transfer reaction is performed as one-pot synthesis reaction subsequent to the sugar chain elongation reaction to produce a sugar chain sialylated at its non-reducing end or a derivative thereof.

In the present specification, the one-pot synthesis refers to a method for synthesizing the compound of interest without isolating or purifying intermediates during the process leading to the synthesis of the compound of interest. The one-pot synthesis reaction for the production of the sugar chain of interest can be performed by the steps of:

(a) performing one or more time(s) a step of reacting a starting material compound with UDP-sugar serving as a substrate of glycosyltransferase in the presence of the glycosyltransferase; and (b) reacting the product of the step (a) with CMP-sialic acid in the presence of sialyltransferase and phosphatase.

In this method, the reaction of the step (a) can involve, for example, a step of producing the biantennary to tetraantennary N-linked complex sugar chain described above.

In the one-pot synthesis reaction, before the start of the sugar transfer reaction of the step (a) (or each sugar transfer reaction in the case of performing a plurality of sugar transfer reactions in the step (a)) or the sialic acid transfer reaction of the step (b), as for the step (a) for example, a concentrated glycosyltransferase solution and a concentrated solution of UDP-sugar serving as a substrate thereof are prepared, and small amounts of these solutions can be added to perform the reaction.

In the one-pot synthesis reaction, heat treatment can be performed after the sugar transfer reaction of the step (a) (or after each sugar transfer reaction and before the start of next sugar transfer reaction in the case of performing a plurality of sugar transfer reactions in the step (a)) to thereby stop the glycosyltransferase-catalyzed sugar transfer reaction in the reaction system. As a result, the yield of the reaction product can be further enhanced. Also, such heat treatment may be performed after the completion of the step (b).

Conditions for the heat treatment are not particularly limited as long as the enzyme is inactivated under the conditions. The heat treatment can be performed, for example, by incubation for a given time at a temperature equal to or higher than 90° C. Preferably, the heat treatment can be performed at approximately 90° C. to 100° C. for approximately 5 to 10 minutes. The heat treatment conditions can be changed appropriately by those skilled in the art.

According to one aspect of the present invention, the sugar chain thus produced can be purified by a well-known method (e.g., HPLC). The HPLC conditions can be set to, for example, conditions described in Examples of the present specification or may be changed appropriately by those skilled in the art according to the structure of the sugar chain.

The terms in the present specification are used for illustrating particular embodiments and are not intended to limit the invention.

The term "comprising" used in the present specification means that described items (members, steps, factors, numbers, etc.) are present and the presence of the other items (members, steps, factors, numbers, etc.) is not excluded therefrom, unless the context evidently requires different interpretation.

All terms (including technical terms and scientific terms) used herein have the same meanings as those understood in a broad sense by those skilled in the art to which the present invention belongs, unless otherwise defined. The terms used herein should be interpreted as having meanings consistent with meanings in the present specification and related technical fields and should not be interpreted in an idealized or excessively formal sense, unless otherwise defined.

The embodiments of the present invention may be described with reference to a schematic diagram. However, such a schematic diagram may be exaggerated for the purpose of clear illustration.

Terms such as "first" or "second" are used for expressing various factors. However, these factors are understood to be not limited by these terms. These terms are used merely for differentiating one factor from the other factors. For example, the first factor may be described as the second factor, and vice versa, without departing from the scope of the present invention.

Hereinafter, the present invention will be described in more detail with reference to Examples. However, the present invention can be embodied in various aspects. Thus, the present invention is not intended to be limited to Examples described herein by any means.

EXAMPLES (1) Expression of ST6Gal-I

The mRNA sequence of human ST6Gal-I is registered under Accession No. X62822 with the public database GenBank. Its amino acid sequence is registered under Accession No. P15907 with GenBank. On the basis of this amino acid sequence, the whole gene was synthesized appropriately for *Ogataea minuta* codon usage. The gene was synthesized so that human ST6Gal-I was expressed in a form except for N-terminal 48 amino acids including the cytoplasmic domain and the transmembrane region. The synthesized gene was flanked by restriction enzyme BamHI sites in order to facilitate introduction into an expression vector. Its sequence is shown in SEQ ID NO: 1. The region containing this sequence was cleaved with BamHI and then introduced to the BamHI site of a methanol-utilizing yeast *Ogataea minuta* expression vector pOMEA1-10H3F to prepare pOMEA1-10H3F-ST6Gal-I. This plasmid pOMEA1-10H3F-ST6Gal-I was cleaved with NotI. Then, an *Ogataea minuta* TK-10-1-2 strain (Δoch1Δpep4Δprb1Δura3Δade1, WO2003/091431) was transformed with the resulting fragment. The transformation was performed using electroporation. The transformed strain was inoculated to an SD-Ade (2% glucose, 0.17% Yeast Nitrogen Base w/o amino acids (manufactured by Difco Laboratories, Inc.), a mixture (20-400 mg/L) of nucleobases except for adenine and amino acids) medium and cultured at 30° C. for 2 days to obtain transformants. Chromosomal integration was confirmed by simple PCR involving dissociating the transformants from the plate and suspending them in a PCR reaction solution. The obtained transformant was designated as a YTY-1 strain.

Next, in order to further improve expression levels, a chaperone gene was introduced to the strain. A vector OnaP11007 containing genes for the constitutive expression of OmPDI1, OmERO1, and OmKAR2 described in Japanese Patent Application No. 2009-539162 was cleaved with NotI, and YTY-1 was transformed with the resulting fragment. The transformation was performed using electroporation. The transformed strain was inoculated to an SD-Ura (2% glucose, 0.17% Yeast Nitrogen Base w/o amino acids (manufactured by Difco Laboratories, Inc.), a mixture (20-400 mg/L) of nucleobases except for uracil and amino acids) medium and cultured at 30° C. for 2 days to obtain transformants. Chromosomal integration was confirmed by simple PCR involving dissociating the transformants from the plate and suspending them in a PCR reaction solution. The obtained transformant was designated as a YTY-2 strain.

The obtained YTY-2 strain was cultured to express ST6Gal-I. Specifically, the strain was inoculated to 5 ml of YPAD+KCl medium (2% polypeptone, 1% yeast extracts, 2% glucose, adenine (40 mg/L), 0.3 M KCl) and precultured overnight at 30° C. Next, 1 ml of the precultured solution was inoculated to 150 ml of YPAD+KCl medium and cultured at 30° C. for 48 hours. The strain was collected, then resuspended in 100 ml of BMMY+2% casamino acid medium (1% yeast extracts, 2% polypeptone, 1.34% Yeast Nitrogen Base w/o amino acids (manufactured by Difco Laboratories, Inc.), 0.1 M KPi (pH 6.0), 2% casamino acid, 0.5% methanol), and cultured at 20° C. for 96 hours. For this culture, methanol was added every 12 hours to achieve the concentration of 0.5%.

After the completion of culture, the strain was removed by centrifugation to prepare a crude enzyme solution.

The crude enzyme solution was dialyzed against an SP buffer (25 mM sodium acetate (pH 5.5), 0.1% Triton X-100) and then applied to HiTrap SP HP (5 ml) equilibrated with an SP buffer. The column was washed with an SP buffer, followed by elution with an SP buffer containing 1 M NaCl. A fraction that exhibited ST6Gal-I activity was collected and dialyzed against a reaction buffer (25 mM MOPS, pH 7.3) to prepare a partly purified sample.

The enzymatic activity was assayed as follows: 2 μl of the crude enzyme solution was added to 18 μl of a reaction solution (0.1 M MOPS (pH 7.3), 5 mM CMP-Neu5Ac, 50 μM PA-Lacto-N-neotetraose (LNnT-PA)) to start reaction. The reaction was performed at 37° C. for 30 minutes and then terminated by boiling. The sample was analyzed by HPLC. The column used was Asahipak NH2P-50 (4.6×250 mm; Shodex, Showa Denko K.K.). The mobile phase used was 0.2 M triethylamine-acetic acid (pH 7.0) (solution A) and acetonitrile (solution B). The column was equilibrated with solution A:solution B=30:70. After sample injection, the ratio of solution A:solution B was linearly changed to 50:50 over 20 minutes for gradient elution. A fluorescence detector (Ex: 315 nm, Em: 380 nm) was used for the detection. The substrate LNnT-PA is eluted at 9 minutes, while the reaction product 6'-Sialyl-LNnT-PA is eluted at 18.5 minutes. The obtained reaction product was quantified from the peak area to determine activity (U). In this context, 1 U is defined as the amount of the enzyme that forms 1 μmol of the reaction product for 1 minute.

(2) Preparation of Asialo Tetraantennary Complex Sugar Chain

A compound represented by the following formula (hereinafter, referred to as NA4-Fmoc) was produced as one type of asialo tetraantennary complex sugar chain derivative by a method shown below:

[Formula 20]

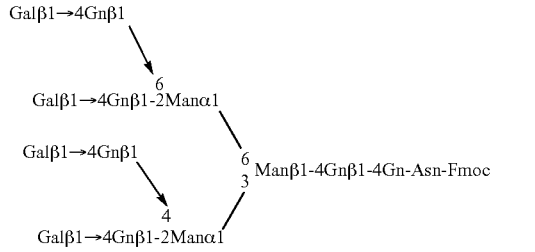

A compound represented by the following formula (hereinafter, referred to as NGA2-Fmoc):

[Formula 21]

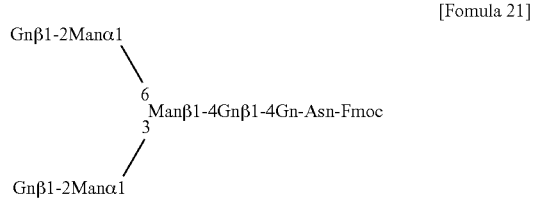

i.e., a compound in which an agalacto biantennary complex sugar chain was linked to the side chain of an asparagine residue and the amino group of the asparagine residue was modified with Fmoc, was used as an acceptor substrate for sugar transfer reaction. 0.3 mU MGAT4a and MGAT5 were added to 0.15 ml of reaction solution A (0.1 M MOPS (pH 7.3), 40 mM UDP-GlcNAc, 6.7 mM NGA2-Fmoc, 10 mM MnCl$_2$, 5 mg/ml bovine serum albumin (BSA), 1 mM PMSF), and the mixture was reacted at 37° C. for 16 hours. The resulting reaction mixture was heat-treated at 100° C. for 5 minutes to inactivate the enzyme. To this solution, equivalent volume of reaction solution B (0.1 M MOPS (pH 7.3), 30 mM UDP-Gal, 10 mM MnCl$_2$, 10 mg/ml BSA, 8 mM AMP) 0.15 ml was added, then 5 mU β4GalT1 was added, and the mixture was reacted at 37° C. for 16 hours. The resulting reaction mixture was heat-treated at 100° C. for 5 minutes to inactivate the enzyme.

The sugar chain (NA4-Fmoc) of interest was purified from the obtained reaction solution. The column used was Kromasil 100-5C18 (4.6×250 mm; Eka Chemicals Inc.). The mobile phase used was 25 mM ammonium acetate (solution A) and acetonitrile (solution B). The column was equilibrated with solution A:solution B=82:18. After sample injection, the sugar chain was collected at 20 minutes. A fluorescence detector (Ex: 265 nm, Em: 315 nm) was used for the detection. The substrate NGA2-Fmoc was eluted as a single peak at 14 minutes, while the reaction product NA4-Fmoc was eluted as a single peak at 8 minutes. The reaction product sugar chain was collected and used as NA4-Fmoc in subsequent experiments.

(3) Preparation of α2,6-Sialylated Tetraantennary Complex Sugar Chain

A compound represented by the following formula (hereinafter, referred to as (α2,6)tetrasialo-NA4-Fmoc):

[Formula 22]

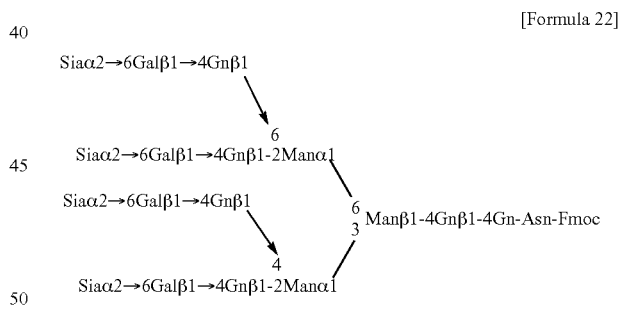

was prepared as one type of α2,6-sialylated tetraantennary complex sugar chain derivative as follows: reaction solution C (0.1 M Tris-HCl (pH 7.5), 1 mM MnCl$_2$, 0.1% Triton X-100, 2 mM CMP-Neu5Ac) containing 50 μM NA4-Fmoc as a starting material was prepared. 160 μU of ST6Gal-I prepared in the paragraph (1) was added to 20 μl of this reaction solution C, and the mixture was reacted at 37° C. for 24 hours. After 0-hour, 1-hour, 6-hour, or 24-hour reaction, each reaction solution was analyzed by HPLC. The results are shown in FIG. 1. The reaction did not completely proceed even after 24 hours, and a sugar chain having 3 sialic acid molecules (hereinafter, referred to as (α2,6)trisialo-NA4-Fmoc; which is abbreviated to "trisialo-" in FIG. 1) was detected as a main peak. Thus, 160 μU ST6Gal-1 and 5 μl of CMP-Neu5Ac (final concentration: 2 mM) were further added to the reaction solution to perform reaction. However, the compound of interest, i.e., the sugar chain having 4 sialic acid molecules ((α2,6)tetrasialo-NA4-Fmoc; which is abbreviated to "tetrasialo-" in FIG. 1) was recovered at a rate of approximately 40%.

The peak corresponding to the sugar chain having 4 sialic acid molecules was collected and used as (α2,6)tetrasialo-NA4-Fmoc in subsequent experiments.

(4) Assay of Sialic Acid-Degrading Activity of ST6Gal-I

No increase was seen in the yield of the reaction product with increase in the amount of the enzyme, suggesting the possibility of degradation of the reaction product. Thus, the following experiment was conducted in order to evaluate whether the reaction product was degraded.

Figure 2:
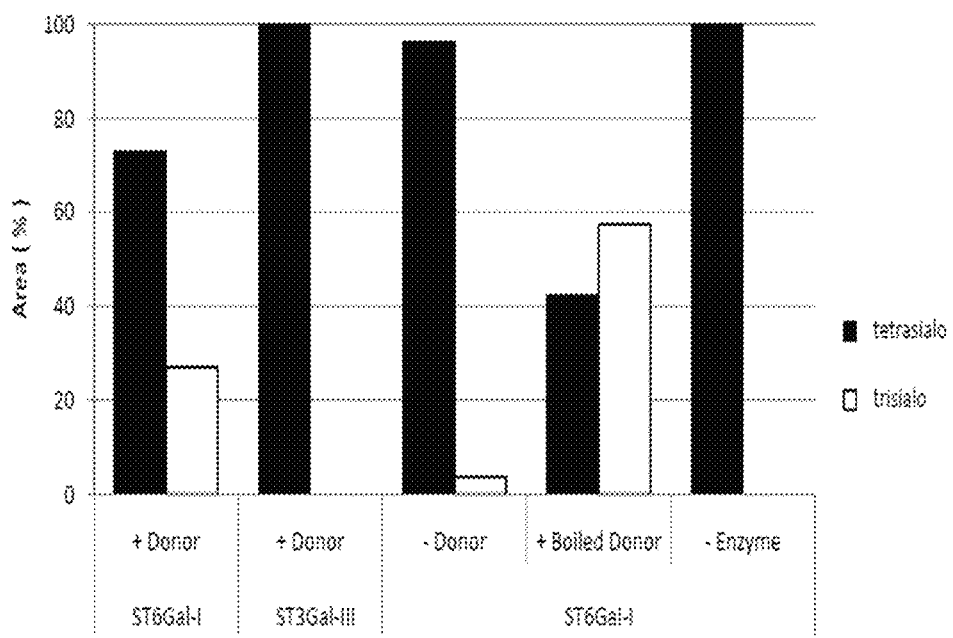
FIG. 2 shows the abundance ratios of (α2,6)tetrasialo-NA4-Fmoc and (α2,6)trisialo-NA4-Fmoc after reaction of the (α2,6)tetrasialo-NA4-Fmoc at 37° C. for 15 hours in the presence or absence of CMP-Neu5Ac and in the presence or absence of sialyltransferase. In the diagram, "+Donor" depicts the results of the reaction in the presence of 2 mM CMP-Neu5Ac; "−Donor" depicts the results of the reaction in the absence of CMP-Neu5Ac; "+Boiled Donor" depicts the results of the reaction in the presence of 2 mM CMP-Neu5Ac after heated at 100° C. for 5 minutes; and "−Enzyme" depicts the results of the reaction in the absence of sialyltransferase.

Reaction solution D (0.1 M Tris-HCl (pH 7.5), 1 mM $MnCl_2$, 0.1% Triton X-100) containing 50 pmol of the sugar chain (α2,6)tetrasialo-NA4-Fmoc was prepared. 5 µl of 50 µU ST6Gal-I was added to 5 µl of the reaction solution D, and the mixture was incubated at 37° C. for 17 hours. Also, a reaction solution supplemented with 50 µU ST6Gal-1 and 5 µl of CMP-Neu5Ac (final concentration: 2 mM) was similarly prepared. Furthermore, a reaction solution supplemented with 50 µU ST6Gal-I and CMP-Neu5Ac (final concentration: 2 mM) heat-treated at 100° C. for 5 minutes was similarly prepared. These solutions were also similarly incubated at 37° C. for 17 hours. Each reaction product was heated at 100° C. for 5 minutes and then analyzed by HPLC in the same way as in the method shown in the paragraph (2). The results are shown in FIG. 2. The elimination of sialic acid was rarely seen in the absence of the substrate donor CMP-Neu5Ac. By contrast, approximately 30% of the (α2,6)tetrasialo-NA4-Fmoc was converted to (α2,6)trisialo-NA4-Fmoc in the presence of CMP-Neu5Ac, demonstrating the elimination of sialic acid. Furthermore, the addition of heated CMP-Neu5Ac caused 58% conversion to (α2,6)trisialo-NA4-Fmoc.

Figure 3:
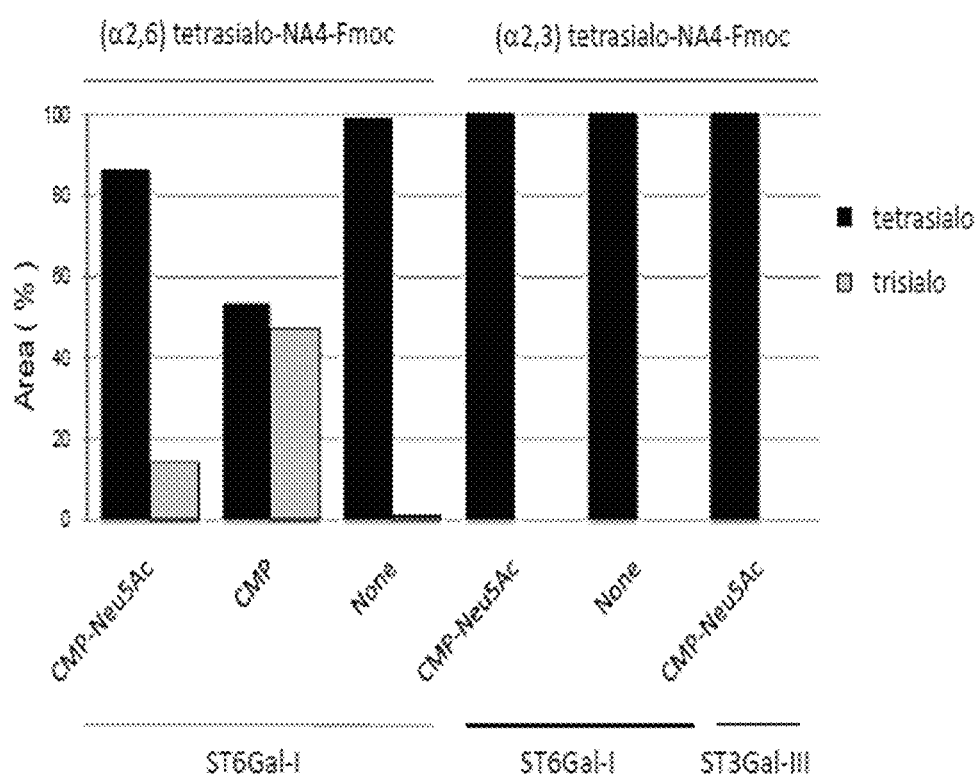
FIG. 3 The left diagram of FIG. 3 shows the abundance ratios of (α2,6)tetrasialo-NA4-Fmoc and (α2,6)trisialo-NA4-Fmoc after reaction of the tetrasialo-NA4-Fmoc with sialyltransferase ST6Gal1 at 37° C. for 15 hours in the presence or absence of CMP-Neu5Ac or CMP. The right diagram of FIG. 3 shows the abundance ratios of (α2,3)tetrasialo-NA4-Fmoc and (α2,3)trisialo-NA4-Fmoc after reaction of the (α2,3)tetrasialo-NA4-Fmoc with sialyltransferase (ST6Gal-I or ST3Gal-III) at 37° C. for 15 hours in the presence or absence of CMP-Neu5Ac.

By contrast, the addition of ST6Gal-I, as shown in FIG. 3, exhibited no degrading activity on (α2,3)tetrasialo-NA4-Fmoc. The addition of α2,3-sialyltransferase ST3Gal-III did not degrade (α2,3)tetrasialo-NA4-Fmoc. This suggested that the elimination of sialic acid by ST6Gal-I was specific for α2,6-linked sialic acid.

(5) Stability of CMP-Neu5Ac

Figure 4:
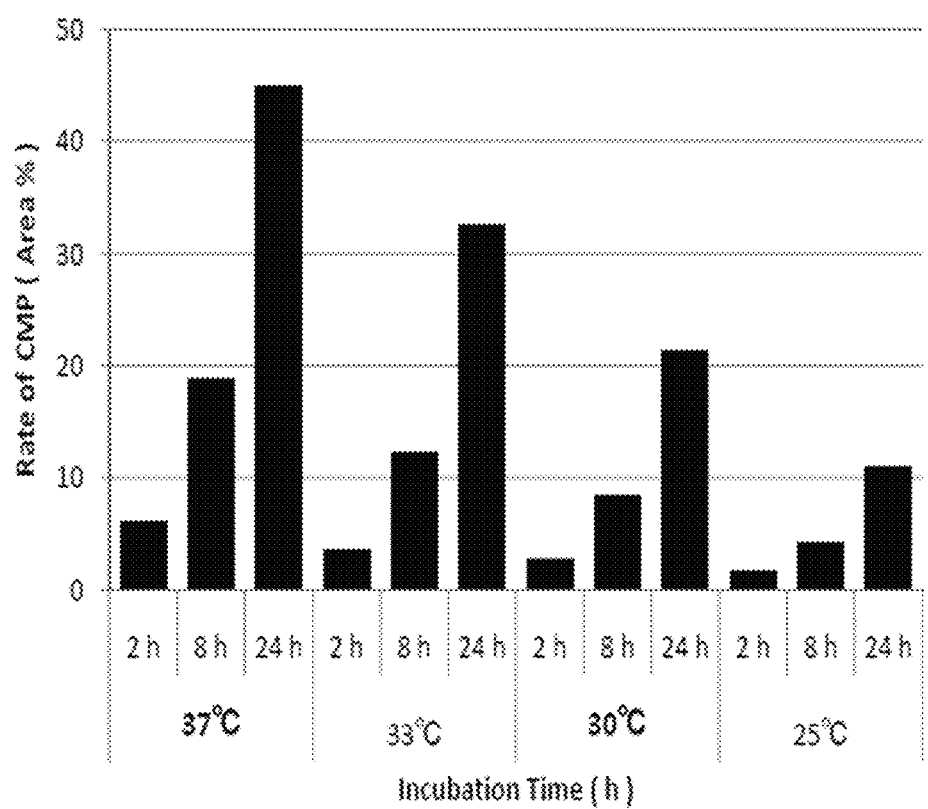
FIG. 4 shows the abundance ratio of CMP after incubation of CMP-Neu5Ac at 37° C., 33° C., 30° C., or 25° C. for 2 hours, 8 hours, or 24 hours.

In order to confirm whether CMP was formed by the degradation of the substrate donor CMP-Neu5Ac, 5 mM CMP-Neu5Ac/0.1 M MOPS (pH 7.3) was incubated at 25° C., 30° C., 33° C., or 37° C., and the amount of CMP formed was measured. The measurement was performed by HPLC using a column TSKgel SuperQ-5PW (7.5×75 mm; Tosoh Corp.) and 50 mM KPi (pH 8.0) as a solvent. A UV detector (detection wavelength: 254 nm) was used for the detection. The degree of CMP formation was indicated by [Peak area of CMP]/[Peak area of CMP+Peak area of CMP-Neu5Ac]×100 (%). The results are shown in FIG. 4. After 24 hours, 45% CMP was formed at 37° C., whereas 21% CMP was formed at 30° C., which was about half of that formed at 37° C. This suggested that the reaction of ST6Gal-I at a lower temperature was able to suppress CMP-dependent sialic acid-degrading activity.

Figure 5:
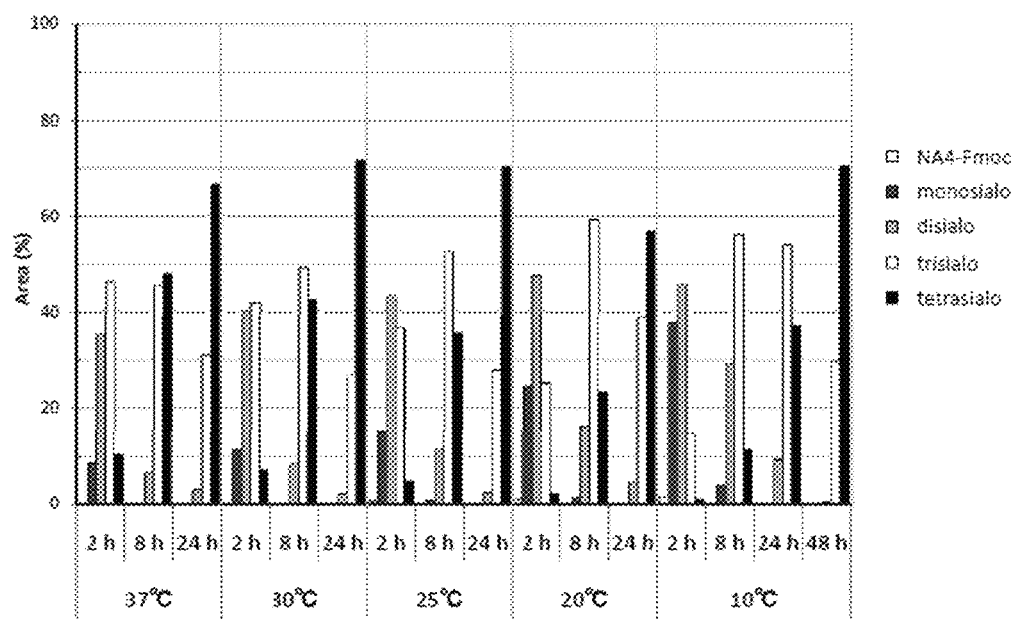
FIG. 5 shows the abundance ratios of (α2,6)tetrasialo-NA4-Fmoc, (α2,6)trisialo-NA4-Fmoc, (α2,6)disialo-NA4-Fmoc, and (α2,6)monosialo-NA4-Fmoc after reaction of NA4-Fmoc with sialyltransferase ST6Gal1 at 37° C., 30° C., 25° C., 20° C., or 10° C. for 2 hours, 8 hours, or 24 hours in the presence of CMP-Neu5Ac.

Next, in order to evaluate the rate of formation of the α2,6-sialylated tetraantennary complex sugar chain, reaction solution E (0.1 M MOPS (pH 7.3), 5 mM $MnCl_2$, 5 mg/ml bovine serum albumin, 5 mM CMP-Neu5Ac) containing 50 µM NA4-Fmoc was prepared. 100 µU of ST6Gal-I prepared in the paragraph (1) was added to 10 µl of the reaction solution E, and the mixture was reacted at 10° C., 20° C., 25° C., 30° C., or 37° C. for 24 hours. As shown in FIG. 5, the yield of the sugar chain (α2,6)tetrasialo-NA4-Fmoc of interest was high after 24-hour reaction at 25° C. and 30° C. This suggested that reaction at 25° C. to 30° C. that fell outside the temperature optimal for sialyltransferase was preferred for enhancing the yield of (α2,6)tetrasialo-NA4-Fmoc.

(6) Establishment of Method for Suppressing Degradation of α2,6-Sialylated Tetraantennary Complex Sugar Chain ((α2,6)Tetrasialo-NA4-Fmoc)

Figure 6:
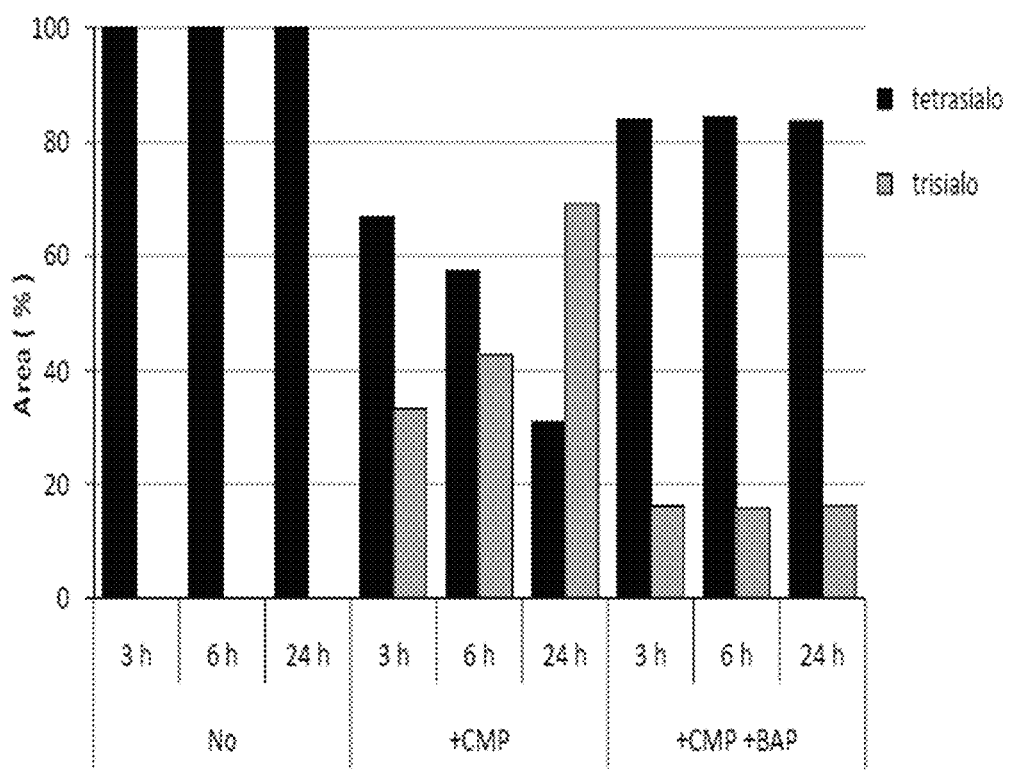
FIG. 6 shows the abundance ratios of (α2,6)tetrasialo-NA4-Fmoc and (α2,6)trisialo-NA4-Fmoc after reaction of the (α2,6)tetrasialo-NA4-Fmoc with sialyltransferase ST6Gal1 at 37° C. for 3 hours, 6 hours, or 24 hours in the absence of CMP and BAP as a control, in the presence of CMP, or in the presence of CMP and BAP.

Since CMP is formed not only by the degradation of the substrate donor CMP-Neu5Ac but as a by-product of the synthesis reaction, an attempt was made to degrade this CMP to thereby suppress the elimination reaction of sialic acid by sialyltransferase. Reaction solution E (0.1 M Tris-HCl (pH 7.5), 1 mM $MnCl_2$, 0.1% Triton X-100) containing 25 pmol of (α2,6)tetrasialo-NA4-Fmoc and 2.5 nmol of CMP was prepared. 25 µU ST6Gal-I was added to 10 µl of this reaction solution E, and the mixture was incubated at 37° C. for 17 hours. Also, a reaction solution supplemented with 25 µU ST6Gal-1 and 50 µU E. coli-derived alkaline phosphatase (BAP) (Takara Bio Inc.) was similarly prepared and incubated in the same way as above. Each reaction product was heated at 100° C. for 5 minutes and then analyzed by the method shown in the paragraph (3). The results are shown in FIG. 6. After 24 hours, approximately 70% of the (α2,6) tetrasialo-NA4-Fmoc was converted to (α2,6)trisialo-NA4-Fmoc in the presence of CMP, demonstrating the elimination of sialic acid. By contrast, the degradation of (α2,6)tetrasialo-NA4-Fmoc was rarely seen in the presence of E. coli-derived alkaline phosphatase (BAP). This demonstrated that CMP can be degraded by phosphatase into 5'-cytidylic acid to thereby suppress the sialic acid-eliminating activity of ST6Gal-I on the tetrasialo sugar chain.

Figure 7:
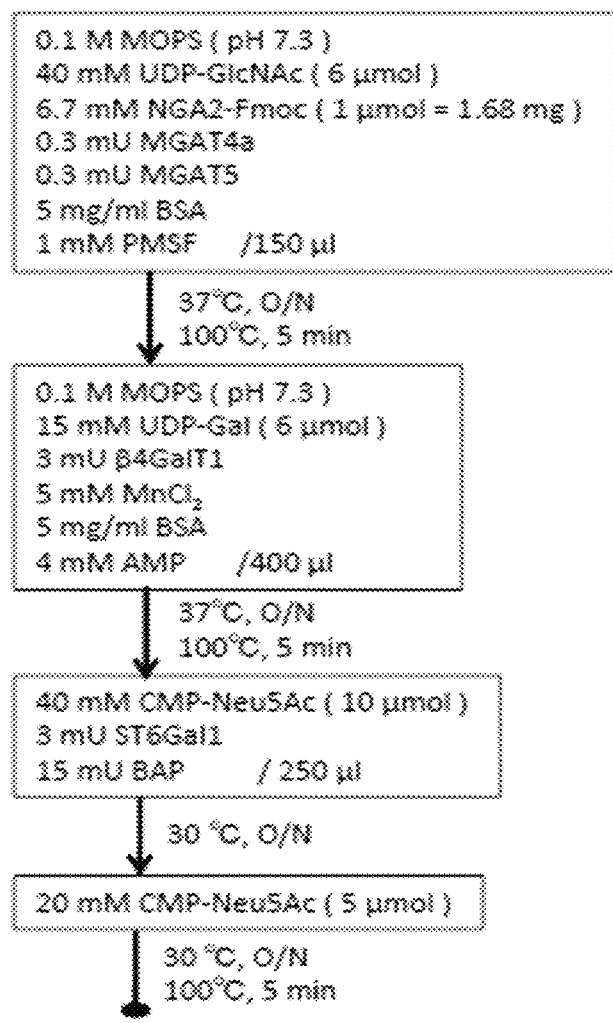
FIG. 7 shows a flow chart of the one-pot synthesis reaction of (α2,6)tetrasialo-NA4-Fmoc described in the paragraph (7) of Examples.
Figure 8:
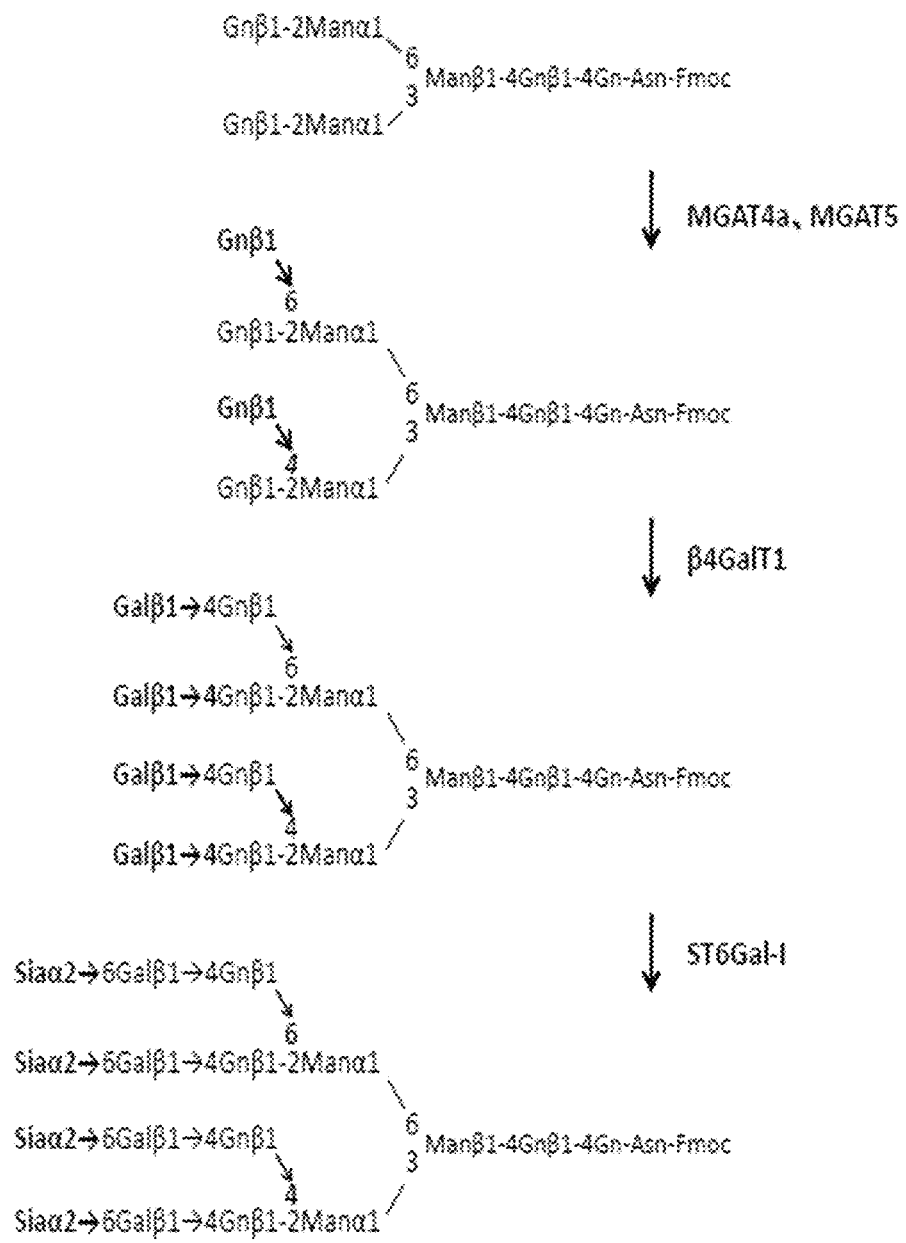
FIG. 8 schematically shows glycosylation reaction using a structural formula in the one-pot synthesis reaction of (α2,6) tetrasialo-NA4-Fmoc described in the paragraph (7) of Examples.

(7) Establishment of Method for One-Pot Synthesis of α2,6-Sialylated Tetraantennary Complex Sugar Chain 150 µl of reaction solution F (0.1 M MOPS (pH 7.3), 40 mM UDP-GlcNAc (6 µmol), 6.7 mM NGA2-Fmoc (1 µmol), 0.3 mU MGAT4a, 0.3 mU MGAT5, 5 mg/ml BSA, 1 mM PMSF) was prepared and reacted at 37° C. for 16 hours. The reaction was terminated by incubation at 100° C. for 5 minutes. Then, 250 µl of reaction solution G (0.1 M MOPS (pH 7.3), 24 mM UDP-Gal (6 µmol), 4.8 mU β4GalT1, 8 mM $MnCl_2$, 5 mg/ml BSA, 4 mM AMP) was added to the reaction solution F, and the mixture was reacted at 37° C. for 16 hours. The reaction was terminated by incubation at 100° C. for 5 minutes, followed by drying under reduced pressure. 250 µl of reaction solution H (40 mM CMP-Neu5Ac (10 µmol), 3 mU ST6Gal-1,15 mU BAP) was added to this tube and reacted at 30° C. for 16 hours. 5 µl of CMP-Neu5Ac (20 mM CMP-Neu5Ac) was further added thereto and reacted at 30° C. for 16 hours. The resulting reaction mixture was heat-treated at 100° C. for 5 minutes to terminate the reaction. A flow chart of this series of one-pot synthesis reaction procedures is shown in FIG. 7. The glycosylation reaction in this series of one-pot synthesis reaction procedures is schematically shown in FIG. 8 using a structural formula.

Figure 9:
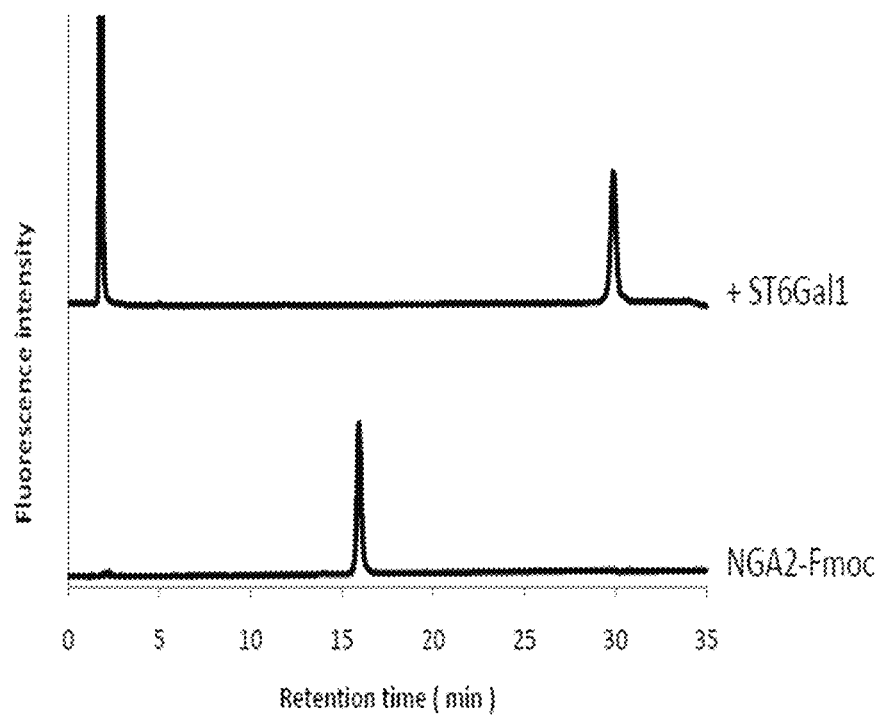
FIG. 9 relates to the one-pot synthesis method of (α2,6) tetrasialo-NA4-Fmoc described in the paragraph (7) of Examples. In the diagram, the upper HPLC chart indicated by "+ST6Gal1" represents an HPLC chart of a reaction product; and the lower HPLC chart indicated by "NGA2-Fmoc" represents an HPLC chart of a starting material for the reaction.

The starting material for the reaction and the reaction product were analyzed by HPLC to quantify (α2,6)tetrasialo-NA4-Fmoc. For the HPLC analysis conditions, the column used was Amido-80 (3 μm, 4.6×150 mm; Tosoh Corp.); the mobile phase used was acetonitrile (solution A) and 0.2 M TEAA (pH 7.0) (solution B); and the column was equilibrated with solution A:solution B=75:25. After sample injection, the sugar chain was collected at 35 minutes. A fluorescence detector (Ex: 265 nm, Em: 315 nm) was used for the detection. The results are shown in FIG. 9. The starting material NGA2-Fmoc for the reaction was eluted as a single peak at approximately 16 minutes, while the reaction product (α2,6) tetrasialo-NA4-Fmoc was eluted as a single peak at approximately 30 minutes. The peak area of the obtained (α2,6) tetrasialo-NA4-Fmoc was 90% with respect to the peak area of the starting material NGA2-Fmoc for the reaction, demonstrating that the sugar chain of interest can be synthesized in very high yields by one-pot synthesis.

INDUSTRIAL APPLICABILITY

The method of the present invention can more efficiently produce a sialic acid-containing sugar chain using sialyltransferase than ever before. Particularly, the method of the present invention can efficiently produce a sialic acid-containing triantennary or tetraantennary complex sugar chain in which sialic acid is linked to each of all non-reducing ends of the antennas, or a derivative thereof, which has previously been difficult to produce. In addition, the production method of the present invention can achieve convenient production in high yields through one-pot synthesis reaction and can achieve even the quantity production of these sugar chains (particularly, (α2,6)tetrasialo tetraantennary complex sugar chains, etc.), which has previously been difficult to achieve. These sugar chains can be used as sugar chains having a novel function or as one type of sugar chain in drugs such as glycoproteins, standards for analytical instruments, scientific reagents, and sugar chain arrays.

The invention claimed is:

1. A method for producing a sialylated second sugar chain or a derivative thereof, comprising reacting a first sugar chain or a derivative thereof with CMP-sialic acid in the presence of ST6Gal-I and phosphatase at a temperature from 25-30° C. for 8 to 48 hours to transfer sialic acid to a non-reducing end of the first sugar chain or a derivative thereof
wherein the sialylated second sugar chain or a derivative thereof is a triantennary or tetraantennary N-linked complex sugar chain, wherein the sugar chain is a compound having sialic acid at each of all non-reducing ends or a derivative thereof.

2. The method according to claim 1, wherein the first sugar chain or a derivative thereof is a triantennary or tetraantennary N-linked complex sugar chain or a derivative thereof.

3. The method according to claim 1, wherein the first sugar chain or a derivative thereof is a compound represented by the following formula:

[Formula 1]

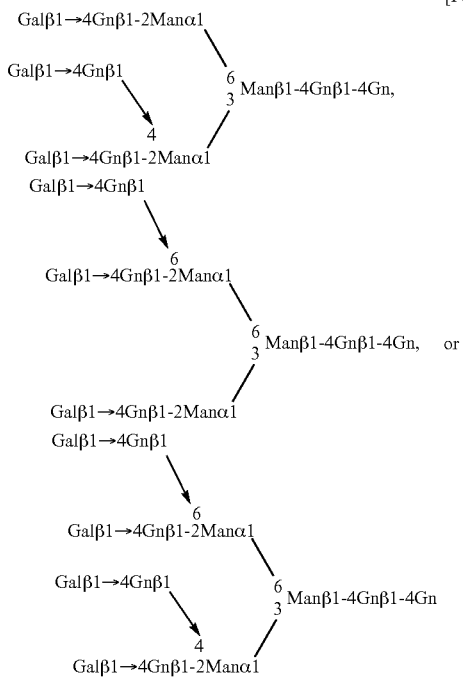

or a derivative thereof.

4. The method according to claim 1, wherein the sialylated second sugar chain or a derivative thereof is a compound represented by the following formula:

Formula 2

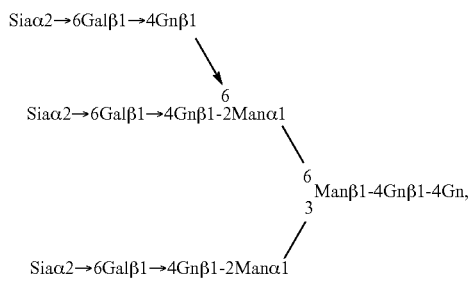

-continued

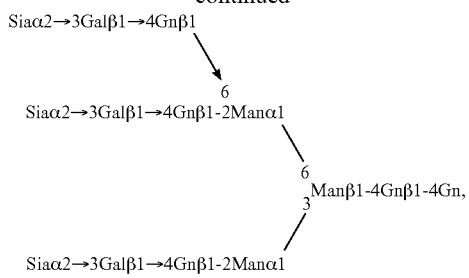

Formula 3

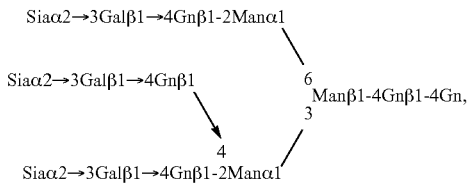

or a derivative thereof.

5. The method according claim 1, wherein the phosphatase is alkaline phosphatase.

6. The method according to claim 1, wherein the phosphatase is *E. coli*-derived alkaline phosphatase.

* * * * *

SEQUENCE LISTING

```
<160> NUMBER OF SEQ ID NOS: 1

<210> SEQ ID NO 1
<211> LENGTH: 1092
<212> TYPE: DNA
<213> ORGANISM: Artificial sequence
<220> FEATURE:
<223> OTHER INFORMATION: a DNA sequence of human ST6Gal-I for the
      synthesis in O. minuta

<400> SEQUENCE: 1
ggatccttga aatctttggg taaattggct atgggttctg attctcaatc tgtttcttca      60
tcttctactc aagatccaca tagaggtaga caaactttgg gttctttgag aggtttggct     120
aaagctaaac cagaagcttc atttcaagtt tggaacaagg attcttcttc taaaaacttg     180
attccaagat tgcaaaagat ttggaagaat tacttgtcta tgaacaagta caaagtttct     240
tataaaggtc caggtccagg tattaagttt tctgctgaag ctttgagatg tcatttgaga     300
gatcatgtta acgtttctat ggttgaagtt actgattttc catttaatac atctgaatgg     360
gaaggttatt tgccaaaaga atctattaga actaaagctg gtccatgggg tagatgtgct     420
gttgtttctt ctgctggttc tttgaaatct tctcaattgg gtagagaaat tgatgatcat     480
gatgctgttt tgagatttaa tggtgctcca actgctaatt tcaacaaga tgttggtact     540 aagactacta ttagattgat gaactctcaa ttggttacta ctgaaaagag attcttgaag     600
gattctttgt acaacgaagg tattttgatt gtttgggacc catctgttta tcattctgat     660
attccaaaat ggtatcaaaa tccagattac aacttcttta caaactacaa gacttacaga     720
aaattgcatc caaatcaacc attttacatt tgaaaccac aaatgccatg ggaattgtgg     780
gatattttgc aagaaatttc tccagaagaa attcaaccaa atccaccatc ttcaggaatg     840
ttgggtatta ttattatgat gactttgtgt gatcaagttg acatttacga atttttgcca     900
tctaaaagaa agactgatgt tgttactac taccaaaagt ttttgattc tgcttgtact     960 atgggtgctt atcatccatt gttgtacgaa aaaaacttgg ttaaacattt gaatcaaggt    1020
actgatgaag acatttactt gttgggtaaa gctactttgc caggttttag aactattcat    1080
tgttaaggat cc                                                        1092
```